(12) United States Patent
Chung et al.

(10) Patent No.: US 10,231,675 B2
(45) Date of Patent: Mar. 19, 2019

(54) METHOD FOR DETECTING BIOMETRIC INFORMATION AND ELECTRONIC DEVICE USING SAME

(71) Applicant: Samsung Electronics Co., Ltd., Suwon-si, Gyeonggi-do (KR)

(72) Inventors: Gihsung Chung, Suwon-si (KR); Jooman Han, Seongnam-si (KR); So Hyun Chung, Seoul (KR); Dae-Yong Lee, Suwon-si (KR); Hongsig Kim, Seongnam-si (KR); Hyunwoo Jang, Suwon-si (KR); Cheolho Cheong, Seoul (KR); Jae-Woong Chun, Suwon-si (KR); Won Suk Choi, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 217 days.

(21) Appl. No.: 15/173,099

(22) Filed: Jun. 3, 2016

(65) Prior Publication Data
US 2017/0042485 A1 Feb. 16, 2017

(30) Foreign Application Priority Data
Aug. 12, 2015 (KR) .......................... 10-2015-0113972

(51) Int. Cl.
*A61B 5/04* (2006.01)
*A61B 5/00* (2006.01)
(Continued)

(52) U.S. Cl.
CPC .......... *A61B 5/7285* (2013.01); *A61B 5/0205* (2013.01); *A61B 5/0402* (2013.01);
(Continued)

(58) Field of Classification Search
USPC .................................................. 600/300–301
See application file for complete search history.

(56) References Cited

U.S. PATENT DOCUMENTS 4,129,125 A 12/1978 Lester et al.
8,942,796 B2 1/2015 Kasama
(Continued)

FOREIGN PATENT DOCUMENTS

EP 2851001 A2 3/2015
EP 2989973 A1 3/2016
(Continued)

*Primary Examiner* — Nicole F Johnson
(74) *Attorney, Agent, or Firm* — Jefferson IP Law, LLP

(57) ABSTRACT

A device for detecting biometric information is provided. The device includes a housing, a fastener coupled to a part of the housing and detachably attached to a part of a user's body, at least one first sensor configured to detect the motion of the electronic device, at least one second sensor configured to detect a change in the user's body, a memory, and a processor electrically connected to the at least one first sensor, the at least one second sensor, and the memory. The memory may store instructions that configure the processor, when being executed, to determine whether the electronic device is worn on a part of the user's body using the at least one first sensor, acquire information on the motion of the electronic device using at least a part of the at least one first sensor for a second period of time shortly before and/or immediately after a first period of time selected passes from the time when the electronic device is worn on a part of the user's body, and activate the at least one second sensor based on at least a part of the information on the motion.

20 Claims, 23 Drawing Sheets

(51) Int. Cl.
  *A61B 5/0205* (2006.01)
  *A61B 5/0402* (2006.01)
  *A61B 5/11* (2006.01)
  *G06F 1/3231* (2019.01)
  *G06F 1/16* (2006.01)
  *G06F 1/3215* (2019.01)
  *G06F 1/3234* (2019.01)
  *G04G 21/02* (2010.01)
  *A61B 5/021* (2006.01)
  *A61B 5/024* (2006.01)
  *A61B 5/145* (2006.01)

(52) U.S. Cl.
  CPC ............... *A61B 5/11* (2013.01); *A61B 5/1118* (2013.01); *A61B 5/443* (2013.01); *A61B 5/6801* (2013.01); *A61B 5/681* (2013.01); *A61B 5/6843* (2013.01); *G04G 21/025* (2013.01); *G06F 1/163* (2013.01); *G06F 1/1684* (2013.01); *G06F 1/1694* (2013.01); *G06F 1/325* (2013.01); *G06F 1/3215* (2013.01); *G06F 1/3231* (2013.01); *A61B 5/021* (2013.01); *A61B 5/02438* (2013.01); *A61B 5/14542* (2013.01); *A61B 2560/0209* (2013.01); *A61B 2562/0219* (2013.01); *A61B 2562/0223* (2013.01); *A61B 2562/0257* (2013.01); *Y02D 10/173* (2018.01)

(56) References Cited

U.S. PATENT DOCUMENTS

| | | |
|---|---|---|
| 2011/0092780 A1 | 4/2011 | Zhang et al. |
| 2015/0057967 A1 | 2/2015 | Albinali |
| 2015/0074797 A1 | 3/2015 | Choi et al. |
| 2015/0223355 A1* | 8/2015 | Fleck ..................... H05K 5/026 |
| | | 361/679.03 |

FOREIGN PATENT DOCUMENTS

| | | |
|---|---|---|
| JP | 2007/209430 A | 8/2007 |
| KR | 10-2015-0046976 A | 5/2015 |
| WO | 2009140360 A1 | 11/2009 |
| WO | 2013043747 A1 | 3/2013 |
| WO | 2014120832 A1 | 8/2014 |

* cited by examiner

METHOD FOR DETECTING BIOMETRIC INFORMATION AND ELECTRONIC DEVICE USING SAME

CROSS-REFERENCE TO RELATED APPLICATION(S)

This application claims the benefit under 35 U.S.C. § 119(a) of a Korean patent application filed on Aug. 12, 2015 in the Korean Intellectual Property Office and assigned Serial number 10-2015-0113972, the entire disclosure of which is hereby incorporated by reference.

TECHNICAL FIELD

The present disclosure relates to an electronic device. More particularly, the present disclosure relates to a device and method for detecting biometric information.

BACKGROUND

Electronic devices have become smaller and slimmer, and have evolved to be easily carried while performing the same or more diverse functions. Although compact electronic devices are generally carried while being received in a user's pocket, they may be worn on the wrist, the head, or the arm of a human body.

In addition, electronic devices may be equipped with biometric sensors (e.g., health care sensors) in order to measure biometric information (e.g., health data) that individuals manage. For example, the biometric information may include blood pressure, a heart rate, an electrocardiogram, skin moisture, saturation of peripheral oxygen, and the like.

The above information is presented as background information only to assist with an understanding of the present disclosure. No determination has been made, and no assertion is made, as to whether any of the above might be applicable as prior art with regard to the present disclosure.

SUMMARY

Electronic devices may operate biometric sensors (e.g., heart rate sensors) in order to measure biometric information (e.g., a heart rate). The operation of the biometric sensors may consume the battery power of the electronic devices. Accordingly, the electronic devices may have difficulty in measuring biometric information for a long period of time (e.g., while users wear the electronic devices).

In another example, when electronic devices measure users' biometric information, the measurement of biometric information is impossible, or the accuracy of the measured biometric information may be deteriorated according to the motion of the electronic devices.

Aspects of the present disclosure are to address at least the above-mentioned problems and/or disadvantages and to provide at least the advantages described below. Accordingly, an aspect of the present disclosure is to provide an electronic device and a method that can selectively operate a biometric sensor based on a selected (or specified) condition.

Another aspect of the present disclosure is to provide an electronic device and a method that can continually (e.g., periodically (e.g., in 1-minute periods)) operate a biometric sensor according to a selected (or specified) period.

Another aspect of the present disclosure is to provide an electronic device and a method that can measure biometric information based on the motion of the electronic device.

In accordance with an aspect of the present disclosure, an electronic device is provided. The electronic device includes a housing, a fastener coupled to a part of the housing and detachably attached to a part of a user's body, at least one first sensor configured to detect a motion of the electronic device, at least one second sensor configured to detect a change in the user's body, a memory, and a processor electrically connected to the first sensor, the second sensor, and the memory, wherein the memory may store instructions that configure the processor, when being executed, to determine whether the electronic device is worn on a part of the user's body using the at least one first sensor, acquire information on the motion of the electronic device using at least a part of the at least one first sensor for a second period of time, which is shorter than the first period of time, shortly before and/or immediately after a first period of time, which is selected (or specified), passes from a time when the electronic device is worn on a part of the user's body, and activate (operate or trigger) the at least one second sensor based on at least a part of the information on the motion.

In accordance with another aspect of the present disclosure, a method of measuring biometric information by an electronic device is provided. The method includes determining whether the electronic device is worn on a part of a user's body using at least one first sensor, activating (operating or triggering) at least one second sensor based on at least a part of the a motion of the electronic device from a time when the electronic device is worn on a part of the user's body to the time when a first period of time selected (or specified) passes, and measuring biometric information based on the at least one second sensor.

Other aspects, advantages, and salient features of the disclosure will become apparent to those skilled in the art from the following detailed description, which, taken in conjunction with the annexed drawings, discloses various embodiments of the present disclosure.

BRIEF DESCRIPTION OF THE DRAWINGS

The above and other aspects, features, and advantages of certain embodiments of the present disclosure will be more apparent from the following description taken in conjunction with the accompanying drawings, in which.

Throughout the drawings, it should be noted that like reference numbers are used to depict the same or similar elements, features, and structures.

DETAILED DESCRIPTION

Figure 1:
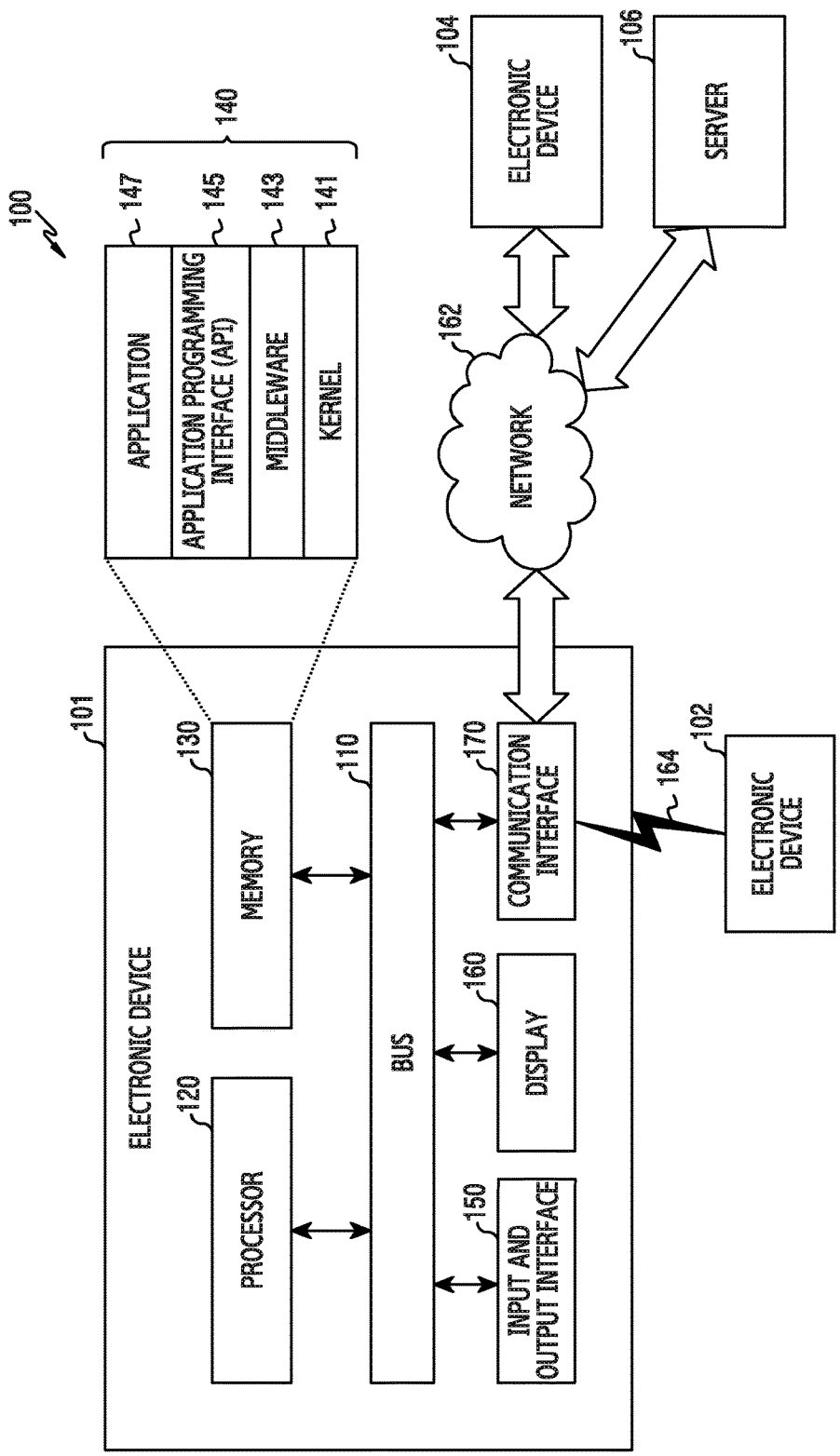
FIG. 1 is a diagram illustrating an electronic device in a network environment according to various embodiments of the present disclosure.

The following description with reference to the accompanying drawings is provided to assist in a comprehensive understanding of various embodiments of the present disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the present disclosure. In addition, descriptions of well-known functions and constructions are omitted for clarity and conciseness.

The terms and words used in the following description and claims are not limited to the bibliographical meanings, but, are merely used by the inventor to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

The terms "have", "may have", "include", or "may include" used in the various embodiments of the present disclosure indicate the presence of disclosed corresponding functions, operations, elements, and the like, and do not limit additional one or more functions, operations, elements, and the like. In addition, it should be understood that the terms "include" or "have" used in the various embodiments of the present disclosure are to indicate the presence of features, numbers, operations, elements, parts, or a combination thereof described in the specifications, and do not preclude the presence or addition of one or more other features, numbers, operations, elements, parts, or a combination thereof.

The terms "A or B", "at least one of A or/and B" or "one or more of A or/and B" used in the various embodiments of the present disclosure include any and all combinations of words enumerated with it. For example, "A or B", "at least one of A and B" or "at least one of A or B" means (1) including at least one A, (2) including at least one B, or (3) including both at least one A and at least one B.

Although the term such as "first" and "second" used in various embodiments of the present disclosure may modify various elements of various embodiments, these terms do not limit the corresponding elements. For example, these terms do not limit an order and/or importance of the corresponding elements. These terms may be used for the purpose of distinguishing one element from another element. For example, a first user device and a second user device all indicate user devices and may indicate different user devices. For example, a first element may be named a second element without departing from the scope of right of various embodiments of the present disclosure, and similarly, a second element may be named a first element.

It will be understood that when an element (e.g., first element) is "connected to" or "(operatively or communicatively) coupled with/to" to another element (e.g., second element), the element may be directly connected or coupled to another element, and there may be an intervening element (e.g., third element) between the element and another element. To the contrary, it will be understood that when an element (e.g., first element) is "directly connected" or "directly coupled" to another element (e.g., second element), there is no intervening element (e.g., third element) between the element and another element.

The expression "configured to (or set to)" used in various embodiments of the present disclosure may be replaced with "suitable for", "having the capacity to", "designed to", "adapted to", "made to", or "capable of" according to a situation. The term "configured to (set to)" does not necessarily mean "specifically designed to" in a hardware level.

Instead, the expression "apparatus configured to . . . " may mean that the apparatus is "capable of . . . " along with other devices or parts in a certain situation. For example, "a processor configured to (set to) perform A, B, and C" may be a dedicated processor, e.g., an embedded processor, for performing a corresponding operation, or a generic-purpose processor, e.g., a central processing unit (CPU) or an application processor (AP), capable of performing a corresponding operation by executing one or more software programs stored in a memory device.

Further, all the terms used herein, including technical and scientific terms, should be interpreted to have the same meanings as commonly understood by those skilled in the art to which the present disclosure pertains, and should not be interpreted to have ideal or excessively formal meanings unless explicitly defined in various embodiments of the present disclosure.

An electronic device according to various embodiments of the present disclosure may be a device. For example, the electronic device according to various embodiments of the present disclosure may include at least one of: a smart phone; a tablet personal computer (PC); a mobile phone; a video phone; an e-book reader; a desktop PC; a laptop PC; a netbook computer; a workstation, a server, a personal digital assistant (PDA); a portable multimedia player (PMP); a Moving Picture Experts Group phase 1 or phase 2 (MPEG-1 or MPEG-2) audio layer 3 (MP3) player; a mobile medical device; a camera; or a wearable device (e.g., a head-mount-device (HMD), an electronic glasses, an electronic clothing, an electronic bracelet, an electronic necklace, an electronic appcessory, an electronic tattoo, a smart mirror, or a smart watch).

In other embodiments, an electronic device may be a smart home appliance. For example, of such appliances may include at least one of: a television (TV); a digital versatile disc (DVD) player; an audio component; a refrigerator; an air conditioner; a vacuum cleaner; an oven; a microwave oven; a washing machine; an air cleaner; a set-top box; a home automation control panel; a security control panel; a TV box (e.g., Samsung HomeSync™, Apple TV™, or Google TV™); a game console (e.g., Xbox™ Play Station™); an electronic dictionary; an electronic key; a camcorder; or an electronic frame.

In other embodiments, an electronic device may include at least one of: a medical equipment (e.g., a mobile medical device (e.g., a blood glucose monitoring device, a heart rate monitor, a blood pressure monitoring device or a temperature meter), a magnetic resonance angiography (MRA) machine, a magnetic resonance imaging (MRI) machine, a computed tomography (CT) scanner, or an ultrasound machine); a navigation device; a global positioning system (GPS) receiver; an event data recorder (EDR); a flight data recorder (FDR); an in-vehicle infotainment device; an electronic equipment for a ship (e.g., ship navigation equipment and/or a gyrocompass); an avionics equipment; a security equipment; a head unit for vehicle; an industrial or home robot; an automatic teller's machine (ATM) of a financial institution, point of sale (POS) device at a retail store, or an internet of things device (e.g., a lightbulb, various sensors, an electronic meter, a gas meter, a sprinkler, a fire alarm, a thermostat, a streetlamp, a toaster, a sporting equipment, a hot-water tank, a heater, or a boiler and the like).

In certain embodiments, an electronic device may include at least one of: a piece of furniture or a building/structure; an electronic board; an electronic signature receiving device; a projector; and various measuring instruments (e.g., a water meter, an electricity meter, a gas meter, or a wave meter).

An electronic device according to various embodiments of the present disclosure may also include a combination of one or more of the above-mentioned devices. Further, it will be apparent to those skilled in the art that an electronic device according to various embodiments of the present disclosure is not limited to the above-mentioned devices.

FIG. 1 is a view illustrating a network environment 100 including an electronic device 101 according to various embodiments of the present disclosure.

Referring to FIG. 1, the electronic device 101 may include a bus 110, a processor 120, a memory 130, an input/output (I/O) interface 150, a display 160, and a communication interface 170.

The bus 110 may be a circuit for connecting the above-described elements (e.g., the processor 120, the memory 130, the I/O interface 150, the display 160 or the communication interface 170, etc.) with each other, and transferring communication (e.g., a control message) between the above-described elements.

The processor 120 may include a CPU, a communication processor (CP), a graphics processing unit (GPU).

The processor 120 may receive, for example, an instruction from the above-described other elements (e.g., the memory 130, the I/O interface 150, the display 160, or the communication interface 170, etc.) via the bus 110, decipher the received instruction, and execute an operation or a data process corresponding to the deciphered instruction.

The memory 130 may include any suitable type of volatile or non-volatile memory. The memory 130 may store an instruction or data received from the processor 120 or other elements (e.g., the I/O interface 150, the display 160, or the communication interface 170, etc.), or generated by the processor 120 or other elements. The memory 130 may include, for example, programming modules 140 such as a kernel 141, a middleware 143, an application programming interface (API) 145, or an application 147. The each of the programming modules may be configured using a software, a firmware, a hardware, or a combination of two or more of these.

The kernel 141 may control or manage system resources (e.g., the bus 110, the processor 120, or the memory 130, etc.) used for executing an operation or a function implemented in the rest of the programming modules, for example, the middleware 143, the API 145, or the application 147. Also, the kernel 141 may provide an interface for allowing the middleware 143, the API 145, or the application 147 to access an individual element of the electronic device 101 and control or manage the same.

The middleware 143 may perform a mediation role so that the API 145 or the application 147 may communicate with the kernel 141 to give and take data. Also, in connection with task requests received from the application 147, the middleware 143 may perform a control (e.g., scheduling or load balancing) for a task request using, for example, a method of assigning priority that may use a system resource (e.g., the bus 110, the processor 120, or the memory 130, etc.) of the electronic device 101 to at least one application 134.

The API 145 is an interface for allowing the application 147 to control a function provided by the kernel 141 or the middleware 143, and may include at least one interface or function (e.g., an instruction) for file control, window control, image processing, or character control, etc.

The I/O interface 150 may transfer an instruction or data input from a user via an I/O unit (e.g., a sensor, a keyboard, or a touchscreen) to the processor 120, the memory 130, or the communication interface 170 via the bus 110, for example. For example, the I/O interface 150 may provide data regarding a user's touch input via the touchscreen to the processor 120. Also, the I/O interface 150 may, for example, output an instruction or data received via the bus 110 from the processor 120, the memory 130, or the communication interface 170 via the I/O unit (e.g., a speaker or a display). For example, the I/O interface 150 may output voice data processed by the processor 120 to a user via a speaker.

The display 160 may include, for example, a liquid crystal display (LCD), a light emitting diode (LED) display, an organic LED (OLED) display, a micro electro mechanical system (MEMS) display, or an electronic paper display. The display 160 may display various types of contents (for example, text, images, videos, icons, or symbols) for users. The display 160 may include a touch screen, and may receive, for example, a touch, gesture, proximity, or hovering input by using an electronic pen or a part of the user's body.

The communication interface 170 may connect communication (e.g., communication 164) between the electronic device 101 and an external device (for example, the electronic device 102, electronic device 104, or the server 106). For example, the communication interface 170 may be connected to a network 162 through wireless communication or wired communication, and may communicate with an external device.

The wireless communication may use at least one of, for example, long term evolution (LTE), LTE-advanced (LTE-A), code division multiple access (CDMA), wideband CDMA (WCDMA), universal mobile telecommunications system (UMTS), wireless broadband (WiBro), and global system for mobile communications (GSM) as a cellular communication protocol.

The wired communication may include, for example, at least one of universal serial bus (USB), high definition multimedia interface (HDMI), recommended standard 232 (RS-232), and plain old telephone service (POTS).

The network 162 may include at least one of communication networks such as a computer network (for example, a local area network (LAN) or a wide area network (WAN)), the internet, and a telephone network.

The electronic devices 102 and 104 may be devices of the same type as that the electronic device 101 or devices of different types from that of the electronic device 101. According to an embodiment, the server 106 may include a group of one or more servers. According to various embodiments, all or some of the operations executed in the electronic device 101 may be carried out in another electronic device or a plurality of electronic devices (for example, the electronic device 102 or 104 and the server 106). According to an embodiment, when the electronic device 101 should perform some functions or services automatically or by a request, the electronic device 101 may make a request for performing at least some functions related to the functions or services to another device (for example, the electronic device 102 or 104, or the server 106) instead of performing the functions or services by itself or additionally. The electronic device (for example, the electronic device 102 or 104, or the server 106) may carry out the functions requested by the electronic device 101 or additional functions and provide results thereof to the electronic device 101. The electronic device 101 may provide the requested functions or services to another electronic device based on the received results or after additionally processing the received results. To this end, for example, cloud computing, distributed computing, or client-server computing technology may be used.

Figure 2:
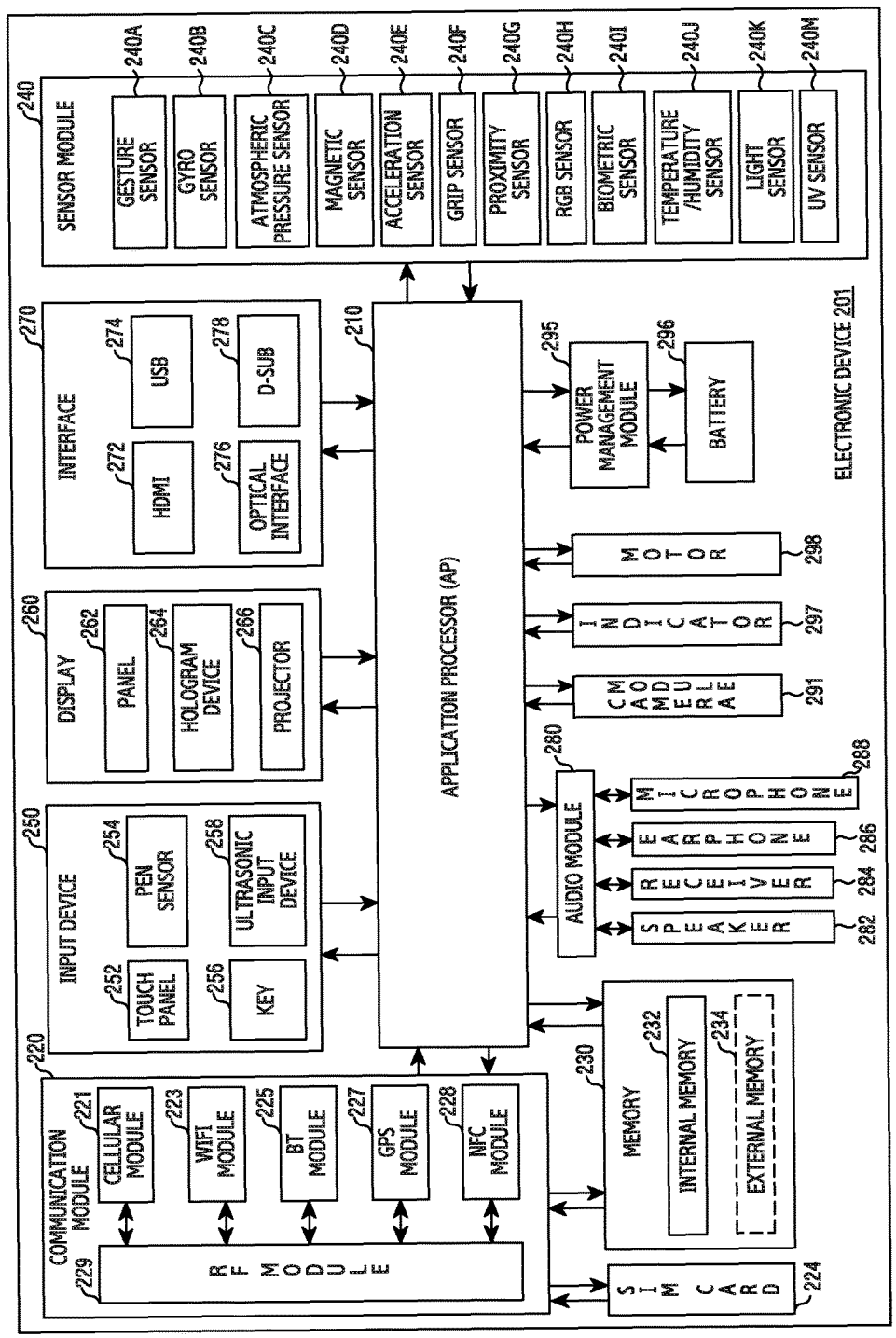
FIG. 2 is a block diagram of an electronic device according to various embodiments of the present disclosure.

FIG. 2 is a block diagram 200 illustrating an electronic device 201 according to various embodiments of the present disclosure. The electronic device 201 may configure, for example, all or a portion of the electronic device 101 illustrated in FIG. 1.

Referring to FIG. 2, the electronic device 201 may include one or more APs 210, a communication module 220, a subscriber identification module (SIM) card 224, a memory 230, a sensor module 240, an input unit 250, a display 260, an interface 270, an audio module 280, a camera module 291, a power management module 295, a battery 296, an indicator 297, or a motor 298.

The AP 210 may drive an OS or an application to control a plurality of hardware or software elements connected to the AP 210, and perform various data processes including multimedia data and operations. The AP 210 may be implemented, for example, as a system on chip (SoC). According to an embodiment, the AP 210 may further include at least one of a GPU or image signal processor (ISP). According to an embodiment, the AP 210 may be implemented to include at least a portion (e.g., the cellular module 221) of the above-described elements. Also, the AP 210 may stores data received from at least one of other elements or generated by at least one of other elements in a non-volatile memory.

The communication module 220 (e.g., the communication interface 170) may perform data transmission/reception in communication between the electronic device 201 (e.g., the electronic device 101) and other electronic devices (e.g., the electronic device 104 or the server 106) connected via a network. According to an embodiment, the communication module 220 may include a cellular module 221, a Wi-Fi module 223, a Bluetooth (BT) module 225, a GPS module 227, a near field communication (NEC) module 228, and a radio frequency (RF) module 229.

The cellular module 221 may provide voice communication, image communication, a short message service, or an internet service, etc. via a communication network (e.g., LTE, LTE-A, CDMA, WCDMA, UMTS, WiBro, or GSM, etc.). Also, the cellular module 221 may perform discrimination and authentication of an electronic device within a communication network using, for example, a subscriber identify module (e.g., a SIM card 224). According to an embodiment, the cellular module 221 may perform at least a portion of functions that may be provided by the AP 210. According to an embodiment, the cellular module 221 may include a CP. Also, the cellular module 221 may be, for example, implemented as an SoC. Though elements such as the cellular module 221 (e.g., a CP), the memory 230, or the power management module 295, etc. are illustrated as elements separated from the AP 210 in FIG. 2, according to an embodiment, the AP 210 may be implemented to include at least a portion (e.g., the cellular module 221) of the above-described elements.

Each of the Wi-Fi module 223, the BT module 225, the GPS module 227, or the NEC module 228 may include, for example, a processor for processing data transmitted/received via a relevant module. Though the cellular module 221, the Wi-Fi module 223, the BT module 225, the GPS module 227, or the NEC module 228 are illustrated as separate blocks in FIG. 2, according to an embodiment, at least a portion (e.g., two or more elements) of the cellular module 221, the Wi-Fi module 223, the BT module 225, the GPS module 227, or the NEC module 228 may be included in one integrated circuit (IC) or an IC package. For example, at least a portion (e.g., a CP corresponding to the cellular module 221 and a Wi-Fi processor corresponding to the Wi-Fi module 223) of processors corresponding to each of the cellular module 221, the Wi-Fi module 223, the BT module 225, the GPS module 227, or the NEC module 228 may be implemented as one SoC.

The RF module 229 may perform transmission/reception of data, for example, transmission/reception of an RF signal. The RF module 229 may include, for example, a transceiver, a power amp module (PAM), a frequency filter, or a low noise amplifier (LNA), etc., though not shown. Also, the RF module 229 may further include a part for transmitting/receiving an electromagnetic wave on a free space in wireless communication, for example, a conductor or a conducting line, etc. Though FIG. 2 illustrates the cellular module 221, the Wi-Fi module 223, the BT module 225, the GPS module 227, and the NEC module 228 share one RF module 229, according to an embodiment, at least one of the cellular module 221, the Wi-Fi module 223, the BT module 225, the GPS module 227, or the NEC module 228 may perform transmission/reception of an RF signal via a separate RF module.

The SIM card 224 may be a card including a subscriber identify module, and may be inserted into a slot formed in a specific position of the electronic device. The SIM card 224 may include unique identify information (e.g., integrated circuit card identifier (ICCID)) or subscriber information (e.g., international mobile subscriber identity (IMSI)).

The memory 230 (e.g., the memory 20) may include an internal memory 232 or an external memory 234. The internal 232 may include, for example, at least one of a volatile memory (e.g., dynamic random access memory (DRAM), static RAM (SRAM), synchronous dynamic RAM (SDRAM)) and a non-volatile memory (e.g., one time programmable read only memory (OTPROM), programmable ROM (PROM), erasable and programmable ROM (EPROM), electrically erasable and programmable ROM (EEPROM), mask ROM, flash ROM, NAND flash memory, NOR flash memory, etc.).

According to an embodiment, the internal memory 232 may be a solid state drive (SSD). The external memory 234 may further include a flash drive, for example, compact flash (CF), secure digital (SD), micro-SD, mini-SD, extreme digital (xD), or a memory stick. The external memory 234 may be functionally connected with the electronic device 201 via various interfaces. According to an embodiment, the electronic device 201 may further include a storage device (or a storage medium) such as a hard drive.

The sensor module 240 may measure a physical quantity or detect an operation state of the electronic device 201, and convert the measured or detected information to an electric signal. The sensor module 240 may include, for example, at least one of a gesture sensor 240A, a gyro sensor 240B, an atmospheric pressure sensor 240C, a magnetic sensor 240D, an acceleration sensor 240E, a grip sensor 240F, a proximity sensor 240G, a color sensor 240H (e.g., red, green, blue (RGB) sensor), a biometric sensor 240I, a temperature/humidity sensor 240J, an illuminance sensor 240K, or an ultra violet (UV) sensor 240M. Additionally or alternatively, the sensor module 240 may include, for example, an E-nose sensor (not shown), an electromyography (EMG) sensor (not shown), an electroencephalogram (EEG) sensor (not shown), an electrocardiogram (ECG) sensor (not shown), an infrared (IR) sensor (not shown), an iris sensor (not shown), or a fingerprint sensor (not shown), etc. The sensor module 240 may further include a control circuit for controlling at least one sensor belonging thereto.

The input unit 250 may include a touch panel 252, a (digital) pen sensor 254, a key 256, or an ultrasonic input unit 258. The touch panel 252 may recognize a touch input using at least one of capacitive, resistive, infrared, or ultrasonic methods. Also, the touch panel 252 may further include a control circuit. A capacitive touch panel may perform detection by a physical contact or proximity recognition. The touch panel 252 may further include a tactile layer. In this case, the touch panel 252 may provide a tactile reaction to a user.

The (digital) pen sensor 254 may be implemented using, for example, a method which is the same as or similar to receiving a user's touch input, or using a separate sheet for detection. The key 256 may include, for example, a physical button, an optical key or keypad. The ultrasonic input unit 258 is a unit for recognizing data by detecting a sound wave using a microphone (e.g., a microphone 288) in the electronic device 201 via an input tool generating an ultrasonic signal, and enables wireless recognition. According to an embodiment, the electronic device 201 may receive a user input from an external device (e.g., a computer or a server) connected to the communication module 220 using the communication module 220.

The display 260 (e.g., the display 160) may include a panel 262, a hologram device 264, or a projector 266. The panel 262 may be, for example, an LCD, or an active-matrix OLED (AM-OLED), etc. The panel 262 may be implemented, for example, such that it is flexible, transparent, or wearable. The panel 262 may be configured as one module together with the touch panel 252. The hologram device 264 may show a three-dimensional image in the air using interferences of light. The projector 266 may project light onto a screen to display an image. The screen may be positioned, for example, inside or outside the electronic device 201. According to an embodiment, the display 260 may further include a control circuit for controlling the panel 262, the hologram device 264, or the projector 266.

The interface 270 may include, for example, a high-definition multimedia interface (HDMI) 272, a USB 274, an optical interface 276, or a D-subminiature (D-sub) 278. The interface 270 may be included, for example, in the communication interface 170 illustrated in FIG. 1. Additionally or alternatively, the interface 270 may include, for example, a mobile high-definition link (MHL) interface, an SD card/multi-media card (MMC) interface, or an infrared data association (IrDA) standard interface.

The audio module 280 may convert a sound and an electric signal in dual directions. At least a partial element of the audio module 280 may be included, for example, in the I/O interface 150 illustrated in FIG. 1. The audio module 280 may process sound information input or output via, for example, a speaker 282, a receiver 284, an earphone 286, or a microphone 288, etc.

The camera module 291 is a device that may shoot a still image and a moving picture. According to an embodiment, the camera module 291 may include one or more image sensors (e.g., a front sensor or a rear sensor), a lens (not shown), an ISP (not shown), or a flash (not shown) (e.g., an LED or xenon lamp).

The power management module 295 may manage power of the electronic device 201. Though not shown, the power management module 295 may include, for example, a power management IC (PMIC), a charger IC, or a battery or a battery or fuel gauge.

The PMIC may be mounted, for example, inside an IC or a SoC semiconductor. A charging method may be classified into a wired charging method and a wireless charging method. The charging IC may charge a battery and prevent introduction of an overvoltage or an overcurrent from a charger. According to an embodiment, the charging IC may include a charging IC for at least one of the wired charging method and the wireless charging method. The wireless charging method may be, for example, a magnetic resonance method, a magnetic induction method, or an electromagnetic wave method, etc., and may additionally include an additional circuit for wireless charging, for example, a circuit such as a coil loop, a resonance circuit, or a rectifier, etc.

The battery gauge may measure, for example, a remnant of the battery 296, a voltage, a current, or a temperature while charging. The battery 296 may store or generate electricity, and supply power to the electronic device 201 using the stored or generated electricity. The battery 296 may include, for example, a rechargeable battery or a solar battery.

The indicator 297 may display a specific state of the electronic device 201 or a portion thereof (e.g., the AP 210), for example, a booting state, a message state, or a charging state, etc. The motor 298 may convert an electric signal to mechanical vibration. Though not shown, the electronic device 201 may include a processor (e.g., a GPU) for supporting a mobile TV. The processor for supporting the mobile TV may process media data corresponding to standards, for example, such as digital multimedia broadcasting (DMB), digital video broadcasting (DVB), or a media flow, etc.

The aforementioned elements of the electronic device according to various embodiments of the present disclosure may be constituted by one or more components, and the name of the corresponding element may vary with a type of electronic device. The electronic device according to various embodiments of the present disclosure may include at least one of the aforementioned elements. Some elements may be omitted or other additional elements may be further included in the electronic device. Further, some of the components of the electronic device according to the various embodiments of the present disclosure may be combined to form a single entity, and thus, may equivalently execute functions of the corresponding elements prior to the combination.

Figure 3:
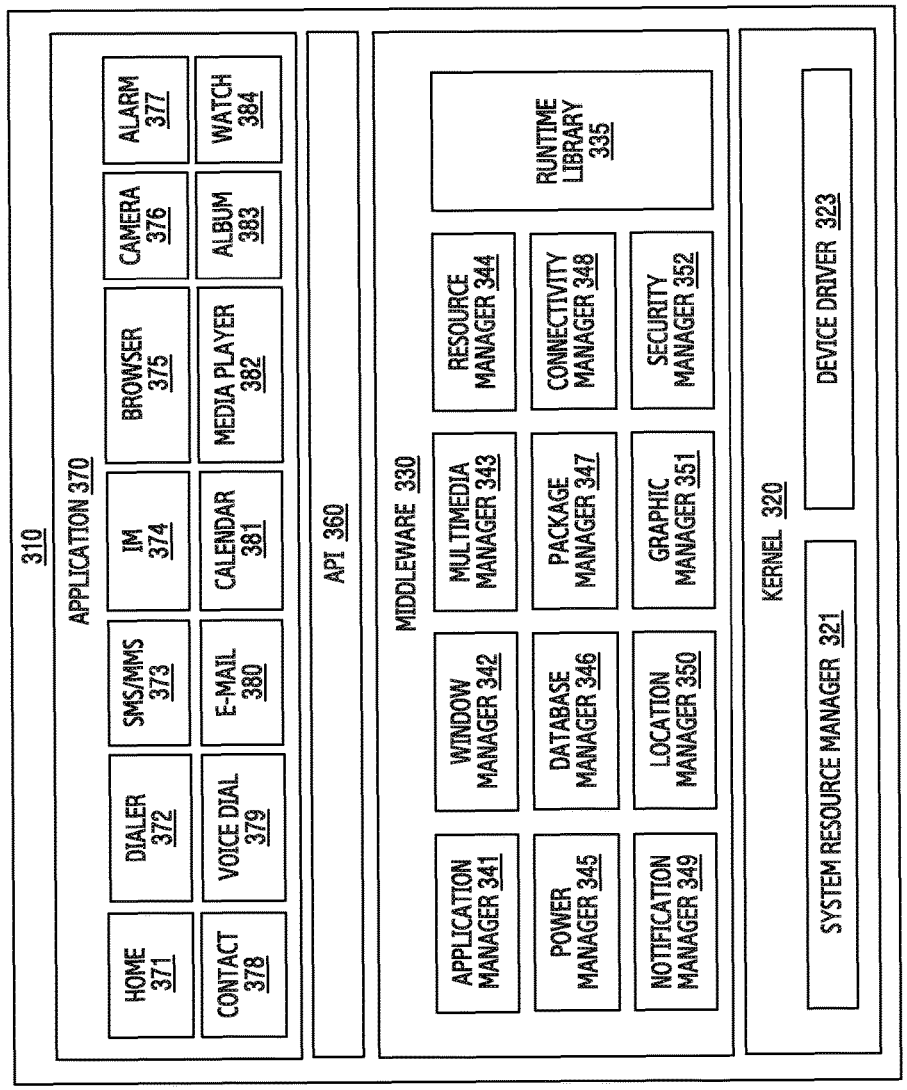
FIG. 3 is a block diagram of a program module according to various embodiments of the present disclosure.

FIG. 3 is a block diagram 300 of a program module 310 according to various embodiments of the present disclosure.

Referring to FIG. 3, the program module 310 (for example, the programming modules 140) may include an operating system (OS) for controlling resources related to the electronic device (for example, the electronic device 101) and/or various applications (for example, the application 147) executed in the operating system. The OS may be, for example, Android, iOS, Windows, Symbian, Tizen, Bada, or the like.

The program module 310 may include a kernel 320, middleware 330, an API 360, and/or applications 370. At least some of the program module 310 may be preloaded in the electronic device or downloaded from the server.

The kernel 320 (for example, the kernel 141 of FIG. 1) may include, for example, a system resource manager 321 or a device driver 323. The system resource manager 321 may control, allocate, or collect the system resources. According to an embodiment, the system resource manager 321 may include a process management unit, a memory management unit, or a file system management unit. The device driver 323 may include, for example, a display driver, a camera driver, a BT driver, a shared-memory driver, a USB driver, a keypad driver, a Wi-Fi driver, an audio driver, or an inter-process communication (IPC) driver.

The middleware 330 may provide a function used by the applications 370 in common or provide various functions to the applications 370 through the API 360 so that the applications 370 can efficiently use limited system resources within the electronic device. According to an embodiment, the middleware 330 (for example, the middleware 143) may include, for example, at least one of a runtime library 335, an application manager 341, a window manager 342, a multimedia manager 343, a resource manager 344, a power manager 345, a database manager 346, a package manager 347, a connectivity manager 348, a notification manager 349, a location manager 350, a graphic manager 351, and a security manager 352.

The runtime library 335 may include, for example, a library module that a compiler uses to add new functions through a programming language while the application 370 is executed. The runtime library 335 may perform I/O management, memory management, or a function for an arithmetic function.

The application manager 341 may manage, for example, a life cycle of at least one of the applications 370. The window manager 342 may manage graphical user interface (GUI) resources used by a screen. The multimedia manager 343 may grasp formats used for the reproduction of various media files, and may perform an encoding or decoding of the media file by using a codec suitable for the corresponding format. The resource manager 344 may manage resources such as a source code, a memory, and a storage space of at least one of the applications 370.

The power manager 345 may operate together with a basic input/output system (BIOS) to manage a battery or power and may provide power information used for the operation of the electronic device. The database manager 346 may generate, search for, or change a database to be used by at least one of the applications 370. The package manager 347 may manage the installation or the updating of applications distributed in the form of package file.

The connectivity manager 348 may manage wireless connection of, for example, Wi-Fi or BT. The notification manager 349 can display or notify of an event such as an arrival message, promise, proximity notification, and the like in such a way that does not disturb a user. The location manager 350 may manage location information of the electronic device. The graphic manager 351 may manage graphic effects to be provided to a user and user interfaces related to the graphic effects. The security manager 352 may provide one or more security functions used for system security or user authentication. According to an embodiment, when the electronic device (for example, electronic device 101) has a call function, the middleware 330 may further include a telephony manager for managing a voice call function or a video call function of the electronic device.

The middleware 330 may include a middleware module for forming a combination of various functions of the aforementioned components. The middleware 330 may provide modules specialized according to types of operating systems in order to provide differentiated functions. Further, the middleware 330 may dynamically remove some of the existing components or add new components.

The API 360 (for example, the API 145) is, for example, a set of API programming functions, and a different configuration thereof may be provided according to an operating system. For example, Android or iOS may provide one API set per platform, and Tizen may provide two or more API sets per platform.

The applications 370 (for example, the application 147) may include, for example, one or more applications which can provide functions such as home 371, dialer 372, short message service (SMS)/multimedia message service (MMS) 373, instant message (IM) 374, browser 375, camera 376, alarm 377, contacts 378, voice dialer 379, email 380, calendar 381, media player 382, album 383, clock 384, health care (for example, measure exercise quantity or blood sugar), or environment information (for example, atmospheric pressure, humidity, or temperature information).

According to an embodiment, the applications 370 may include an application (hereinafter, referred to as an "information exchange application" for convenience of the description) supporting information exchange between the electronic device (for example, the electronic device 101) and an external electronic device. The information exchange application may include, for example, a notification relay application for transferring predetermined information to an external electronic device or a device management application for managing an external electronic device.

For example, the notification relay application may include a function of transferring, to the external electronic device, notification information generated from other applications of the electronic device 101 (for example, an SMS/MMS application, an e-mail application, a health management application, or an environmental information application). Further, the notification relay application may receive notification information from, for example, a control device and provide the received notification information to the user. The device management application may manage (for example, install, delete, or update), for example, a function for at least a part of the external electronic device communicating with the electronic device (for example, turning on/off the external electronic device itself (or some elements thereof) or adjusting brightness (or resolution) of a display), applications executed in the external electronic device, or services provided from the external electronic device (for example, a telephone call service or a message service).

According to an embodiment, the applications 370 may include an application (for example, health management application) designated according to attributes of the external electronic device (for example, attributes of the electronic device such as the type of electronic device which corresponds to a mobile medical device). According to an embodiment, the applications 370 may include an application received from the external electronic devices (for example, the server or the electronic device). According to an embodiment, the applications 370 may include a preloaded application or a third party application which can be downloaded from the server. The names of the components of the program module 310 according to the embodiment illustrated in FIG. 3 may vary according to the type of operating system.

According to various embodiments, at least some of the program module 310 may be implemented by software, firmware, hardware, or a combination of two or more thereof. At least some of the program module 310 may be implemented (for example, executed) by, for example, the processor (for example, the application program). At least some of the program module 310 may include, for example, a module, program, routine, sets of instructions, or process for performing one or more functions.

Figure 4A:
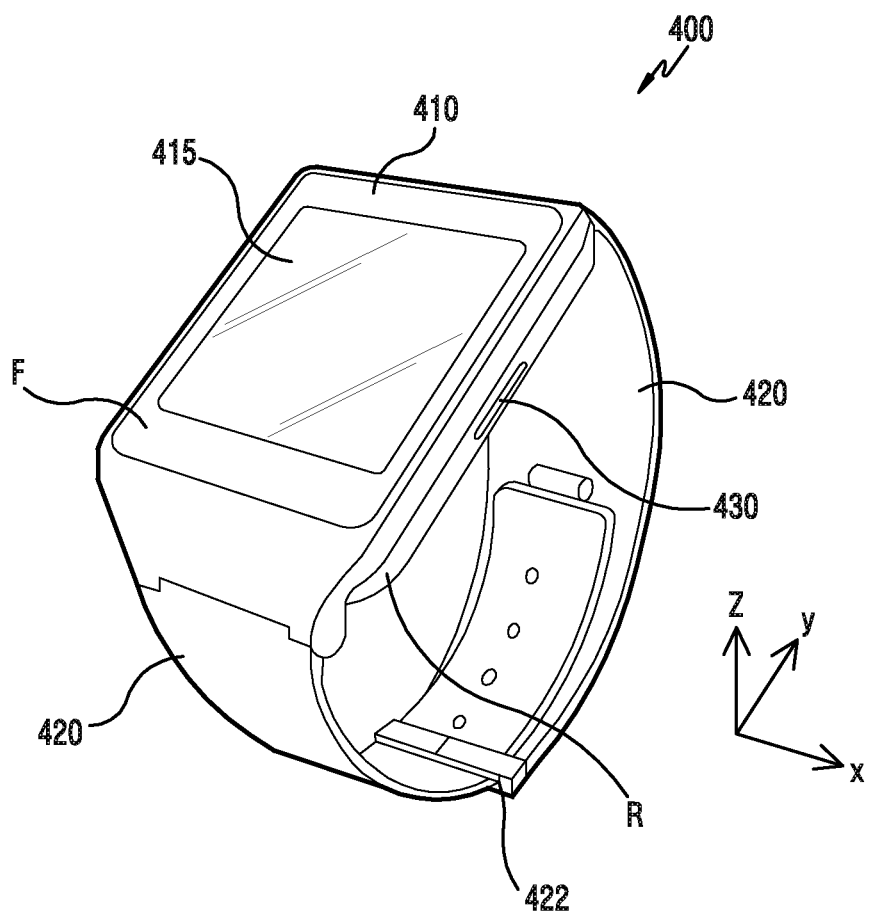
FIGS. 4A, 4B, and 4C are views illustrating an electronic device according to various embodiments of the present disclosure.
Figure 4B:
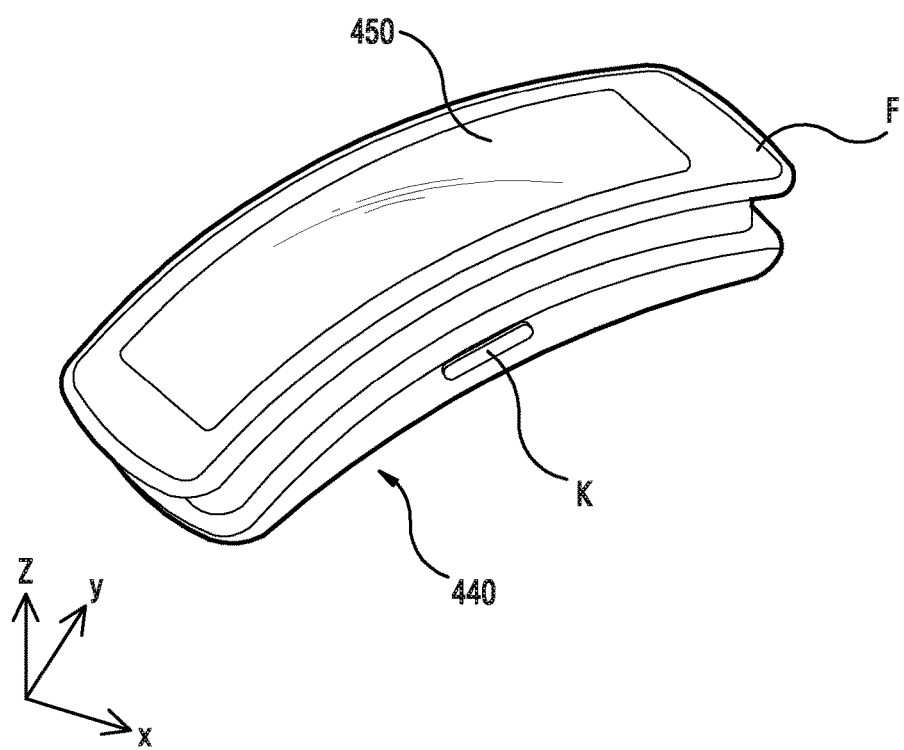
Figure 4C:
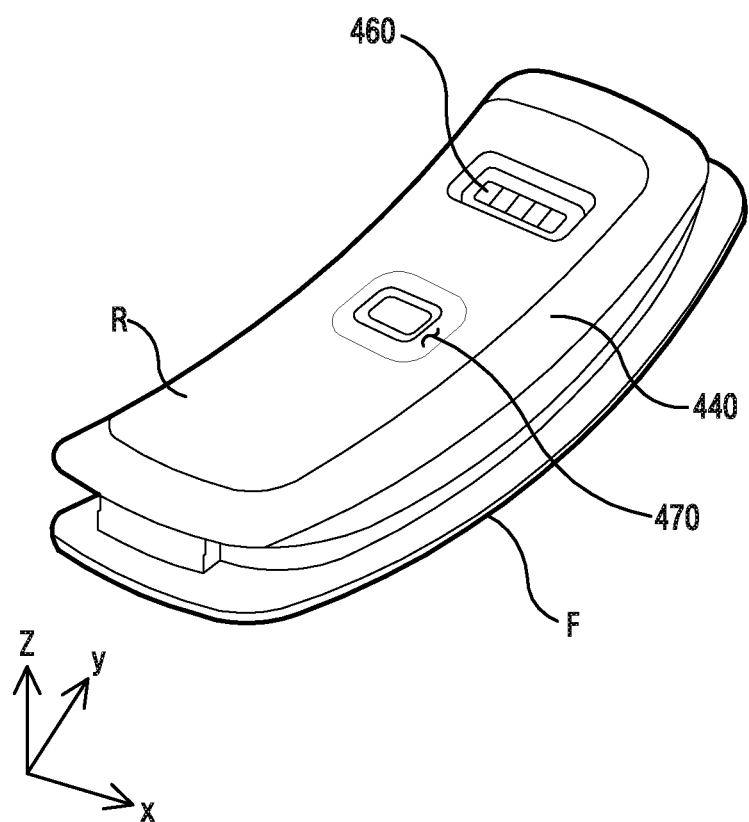

FIGS. 4A, 4B, and 4C are views illustrating an electronic device according to various embodiments of the present disclosure.

A three-dimensional X-Y-Z Cartesian coordinate system is illustrated in FIGS. 4A, 4B, and 4C, where the 'Z-axis' may denote the vertical direction (thickness direction) of the main body of the electronic device; the 'X-axis' may denote the lateral direction of the main body; and the 'Y-axis' may denote the longitudinal direction of the main body.

FIG. 4A is a perspective view of the electronic device according to various embodiments of the present disclosure.

Referring to FIG. 4A, the electronic device 400 (e.g., the electronic device 101 of FIG. 1) may be a wrist-mounted wearable electronic device that can be worn on a user's wrist. However, the various embodiments of the present disclosure are not limited thereto, and the electronic device may also be one of a bracelet, a strip, a band, an attachment type (band-aid type) band, a belt, ear-mounted earphones, headphones, a clothing type electronic device, a shoe type electronic device, an HMD, a hat type electronic device, a glove type electronic device, a finger-tip type electronic device, a clip type electronic device, an arm band type electronic device, a contact lens device, digital clothing, and a remote controller.

According to various embodiments, the electronic device 400 may include the main body 410 and connection parts 420 (e.g., straps) that are equipped to the main body 410.

According to various embodiments, the electronic device 400 may have a battery (e.g., a rechargeable battery, etc.) therein as a power supply means. For example, the electronic device 400 may be implemented to be selectively mounted on a portable charging cradle in order to recharge the battery.

According to various embodiments, the main body 410 may include a display 415, at least one key button 430 (e.g., a side key K, a touch sensor, or a pressure sensor), a sensor module (e.g., a biometric sensor, etc.), and/or the like. According to various embodiments, the display 415 may include a touch screen to receive a touch input. According to an embodiment, the main body 410 may include the front surface F and the rear surface R which makes contact with the user's body while the main body 410 is worn on the user's body. For example, the display 415 may be disposed on the front surface F of the main body 410, and the sensor module may be disposed on the rear surface R of the main body 410. However, the various embodiments of the present disclosure are not limited thereto, and the display 415 or the sensor module may be disposed in various regions of the electronic device 400. For example, the sensor module may also be disposed on the connection parts 420.

According to various embodiments, the main body 410 may have a bar shape and may at least partially have a curvature that corresponds to the user's body. For example, the main body 410 may have a curved rectangular shape extending in the longitudinal direction (Y-axis direction). According to an embodiment, the main body 410 may have fastening recesses formed on opposite sides thereof with which the connection parts 420 are engaged.

According to various embodiments, the connection parts 420 may be configured to be coupled to, or separated from, the main body 410. According to various embodiments, the connection parts 420 may be formed of a resilient material. Accordingly, it is possible to bring the main body 410 close to the skin of the user's body. According to an embodiment, the connection parts 420 may have a changeable structure and may be implemented in various designs or colors. Accordingly, the user may change the connection parts 420 according to his/her preference.

According to various embodiments, the connection parts 420 may be coupled to the main body 410 and may include a fastener 422 that enables the connection parts 420 to be detachably attached to a part of the user's boy. According to an embodiment, the electronic device 400 may be worn on the wrist by a method of tying and fastening the connection parts 420 together while the electronic device 400 is placed on the wrist. For example, one of the connection parts 420 may have a plurality of openings for wrist adjustment that are formed therein at a constant interval, and the other connection part 420 may include the fastener 422 that is coupled through one of the openings for wrist adjustment.

According to various embodiments, the main body 410 may have a rotary body (not illustrated) (e.g., a rotary input module) mounted thereon for adjusting various user interface environments that are displayed on the display 415. According to various embodiments, the rotary body may have a protrusion shape similar to a crown and may be rotatably disposed on the side surface of the main body 410. According to various embodiments, in a case where the main body 410 has a circular shape, the rotary body may be rotatably mounted on the top, bottom, or side surface of the main body 410. For example, the rotary body may be disposed on a bezel that surrounds the edge of the display 415 that is disposed on the top of the main body 410.

FIG. 4B is a perspective view of the main body of the electronic device 400 according to various embodiments of the present disclosure, and FIG. 4C is a perspective view of the main body of the electronic device 400 according to various embodiments of the present disclosure, when viewed in a different direction.

Referring to FIGS. 4B and 4C, the main body may include a main body housing 440 and a display 450 mounted on the main body housing 440. According to various embodiments, the main body housing 440 may have the front surface F, the rear surface R, and the side surface that connects the front surface F and the rear surface R. However, the various embodiments of the present disclosure are not limited thereto, and the main body housing 440 may be constituted by the front surface F and the rear surface R. Furthermore, the front surface F, the rear surface R, and the side surface of the main body housing 440 may be integrally formed with each other. According to an embodiment, the front surface F and the rear surface R may be configured to have different curvatures.

According to various embodiments, the main body housing 440 may further include a key button (e.g., the key button 430, the side key K, a touch sensor, or a pressure sensor) for inputting various types of information. According to an embodiment, the front surface F may be a surface on which the display 450 is mounted, and the rear surface R may be a wearing surface that makes contact with the user's body. However, the various embodiments of the present disclosure are not limited thereto, and the display 415 or the sensor module may be disposed in various regions of the electronic device 400.

According to various embodiments, the display 450 may be disposed on the front surface F of the main body housing 440. Accordingly, it may be easy for the user to view a screen displayed through the electronic device. The display 450 is illustrated in a shape that reflects the curved surface of the user's body, but may be constituted by a flat panel display (e.g., an LCD, an OLED, etc.), a curved display, or a flexible display. For example, in the specific embodiments of the present disclosure, the main body 410 is illustrated as including a curved display, but the main body 410 may include a flat panel display or a flexible display.

Referring to FIG. 4C, a sensor module 470 (e.g., a biometric sensor) may be disposed on the rear surface R of the main body housing 440 according to an embodiment. For example, the sensor module may have a shape that is brought close to the user's wrist. Accordingly, it is possible to enhance the comfort that the user experiences when wearing the electronic device.

The sensor module 470 (e.g., the sensor module 240 or the biometric sensor) provided in the main body housing 440 may include at least one of an acceleration sensor, a gyro sensor, a terrestrial magnetism sensor, a heart rate sensor, a proximity sensor, an optical sensor, a galvanic skin response (GSR) sensor, an ECG sensor, an EMG sensor, a blood glucose sensor, a blood pressure sensor, a pressure sensor, and a temperature sensor. In addition, the sensor module may also include other sensors that detect a sensing value for determining whether the electronic device 400 is worn. According to various embodiments, the sensor module 470 may be provided on the rear surface R of the main body housing 440 in a single module shape that includes: a sensor (e.g., an acceleration sensor, a terrestrial magnetism sensor, or a gyro sensor) for measuring the motion of the electronic device 400; a sensor (e.g., a proximity sensor or a pressure sensor) that is used to determine whether the electronic device 400 is worn on a body; and a biometric sensor (e.g., a heart rate sensor, a blood pressure sensor, or a body temperature sensor) for measuring a biometric signal.

According to various embodiments, connection members 460 (e.g., a charging terminal, the interface 270, etc.) may be disposed on the rear surface R of the main body housing 440.

Figure 5A:
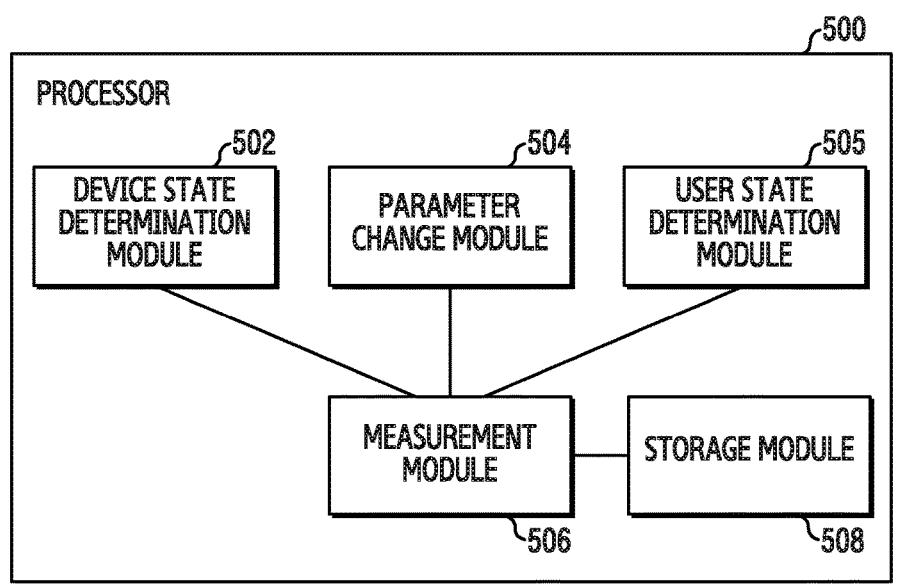
FIG. 5A is a diagram illustrating the configuration of a processor according to various embodiments of the present disclosure.

FIG. 5A is a diagram illustrating the configuration of a processor 500 according to various embodiments of the present disclosure. According to various embodiments, the processor may be a processor (e.g., the processor 120) of an electronic device (e.g., the electronic device 101 or 400).

Referring to FIG. 5A, the processor 500 may include a device state determination module 502, a parameter change module 504, a user state determination module 505, a measurement module 506, and a storage module 508.

According to various embodiments, the device state determination module 502 may determine the state of the electronic device (e.g., a wearing or non-wearing state, a proximity or non-proximity state, or an in-use (holding) or not-in-use (non-holding) state). According to various embodiments, the device state determination module 502 may determine the state of the electronic device based on at least one sensor. According to an embodiment, the device state determination module 502 may determine the state of the electronic device based on information acquired through at least one of an acceleration sensor, a terrestrial magnetism sensor, a gyro sensor, a proximity sensor, an atmospheric pressure sensor (or a pressure sensor), and a temperature sensor.

For example, when the motion of the electronic device is detected through, for example, an acceleration sensor, a terrestrial magnetism sensor, or a gyro sensor, the device state determination module 502 may determine that the electronic device has been worn on a user's body. Furthermore, when the motion of the electronic device is not detected through, for example, an acceleration sensor, a terrestrial magnetism sensor, or a gyro sensor, the device state determination module 502 may determine that the electronic device has not been worn on the user's body.

For example, when an object (e.g., a user) is detected within a selected (or specified) distance (e.g., about 10 cm) from the electronic device through, for example, a proximity sensor, the device state determination module 502 may determine that the electronic device is close to the object (e.g., the electronic device is used or held by the user). Further, when an object (e.g., a user) is not detected within a selected (or specified) distance from the electronic device through, for example, a proximity sensor, the device state determination module 502 may determine that the electronic device is not close to the object (e.g., the electronic device is not used or held by the user).

For example, when a selected (or specified) pressure or a selected (or specified) temperature (e.g., about 37 degrees Celsius) is detected through, for example, a pressure sensor or a temperature sensor, the device state determination module 502 may determine that the electronic device is used or held by a user. Further, when a selected pressure or a selected temperature is not detected through a pressure sensor or a temperature sensor, the device state determination module 502 may determine that the electronic device is not used or held by the user.

According to various embodiments, the device state determination module 502 may determine the state of the electronic device based on whether the electronic device is electrically or mechanically connected or not. For example, in a case where the electronic device is a pair of smart eyeglasses, a switch circuit included in the smart eyeglass temples may be connected when the smart eyeglasses are worn on a user's head. Accordingly, the device state determination module 502 may determine the state of the electronic device to be a wearing state. Further, in a case where the smart eyeglasses are not worn on the user's head, the switch circuit included in the smart eyeglass temples may not be connected. Accordingly, the device state determination module 502 may determine the state of the electronic device to be a non-wearing state.

For example, in a case where the electronic device is a smart watch, the device state determination module 502 may determine the state of the electronic device to be a wearing state when the buckle of the smart watch is connected. Further, the device state determination module 502 may determine the state of the electronic device to be a non-wearing state when the buckle of the smart watch is not connected.

According to various embodiments, the user state determination module 505 may determine a user's state (e.g., a sleep state). According to an embodiment, the user state determination module 505 may determine the user's state based on the user's pattern. For example, the user's pattern may include the user's motion pattern, a life pattern relating to a specified schedule, etc.

According to various embodiments, the user state determination module 505 may determine, for example, the user's motion, the strength of the motion, etc. when biometric information is measured. For example, the user state determination module 505 may determine the user's state to be a sleep state when the user's motion strength is lower than a selected (or specified) strength. Further, the user state determination module 505 may determine the user's state to be an active state (e.g., a state in which the user does not sleep) when the user's motion strength is higher than, or equal to, the selected (or specified) strength. According to an embodiment, the user state determination module 505 may provide information on the user's motion to the measurement module 506 or the parameter change module 504 in order to change a biometric information measurement method.

According to various embodiments, the user state determination module 505 may determine the user's state based on schedule information stored in the electronic device. For example, a first time (e.g., from about 11:00 P.M. to about 8:00 A.M.) may be specified as a 'sleeping time,' and a second time may be specified as an 'active time' (e.g., from about 8:00 A.M. to about 11:00 P.M.) in the schedule stored in the electronic device. In this case, the user state determination module 505 may determine the user's state at the first time to be a 'sleep state' based on the schedule. Further, the user state determination module 505 may determine the user's state at the second time to be an 'active state' based on the schedule.

According to various embodiments, the measurement module 506 may measure a user's biometric information. According to various embodiments, the measurement module 506 may measure biometric information based on at least one sensor. According to an embodiment, the measurement module 506 may measure at least one of a blood pressure, a heart rate, an ECG, skin moisture, saturation of peripheral oxygen, a body temperature, blood glucose, an EEG, an EMG, and the like based on a sensor that is brought into contact with at least a part of a body. According to various embodiments, the measurement module 506 may be activated when the state of the electronic device is determined to be a selected (or specified) state (e.g., a wearing state) through the device state determination module 502.

According to various embodiments, the measurement module 506 may perform a measurement operation when a biometric information measurement period (e.g., about 1 minute) arrives. According to various embodiments, the measurement module 506 may perform the measurement operation based on the motion of the electronic device or a user when the biometric information measurement period arrives. According to an embodiment, when the measurement period arrives, the measurement module 506 may identify the motion of the user or the electronic device that was measured before the period arrives, and when the motion satisfies a selected (or specified) condition (e.g., when the strength of the motion is lower than a selected (or specified) strength), the measurement module 506 may measure biometric information. According to another embodiment, when the motion of the electronic device or the user does not satisfy the selected (or specified) condition (e.g., when the strength of the motion is higher than the selected (or specified) strength), the measurement module 506 may monitor a change in the motion for a predetermined period of time (e.g., about 10 seconds) with respect to the time when the period arrives. According to an embodiment, when the change in the motion for the selected (or specified) period of time satisfies the selected (or specified) condition (e.g., when the average of motion data is smaller than a selected (or specified) value), the measurement module 506 may measure biometric information.

According to various embodiments, the parameter change module 504 may change a measurement parameter used for measuring biometric information. According to an embodiment, the parameter change module 504 may change the light-emitting time, the biometric information measurement period, the sampling rate, the biometric information measurement trigger, the motion determination condition, etc. of at least one sensor. Accordingly, it is possible to reduce power consumption that is generated when the electronic device measures biometric information, or to enhance the accuracy of measurement of biometric information. Further, according to an embodiment, when biometric information is measured, the parameter change module 504 may change a measurement parameter based on situation information that is associated with the motion strength of the electronic device or a body, the physical characteristic or state of an object to be measured, a measurement quality, a measurement result, or the like while the biometric information is being measured.

According to various embodiments, the storage module 508 may store at least one program for the operation of the electronic device. The storage module 508 may store information for the operation of at least one of the device state determination module 502, the parameter change module 504, the user state determination module 505, and the measurement module 506. According to various embodiments, the device state determination module 502, the parameter change module 504, the user state determination module 505, the measurement module 506, or the storage module 508 may be at least one software element.

According to various embodiments, the processor 500 may include at least one of the device state determination module 502, the parameter change module 504, the user state determination module 505, the measurement module 506, and the storage module 508 in order to perform the above-described measurement operations.

Although not illustrated, according to various embodiments, the device state determination module 502, the parameter change module 504, the user state determination module 505, the measurement module 506, and the storage module 508 may be included in a plurality of processors (or chips). For example, the device state determination module 502 and the user state determination module 505 may be included in a first processor (or a first chip). The parameter change module 504 may be included in a second processor (or a second chip). Further, the measurement module 506 may be included in a third processor (or a third chip).

According to various embodiments, the electronic device may perform the above-described operation of measuring biometric information through a separate module that is different from the processor 500.

Figure 5B:
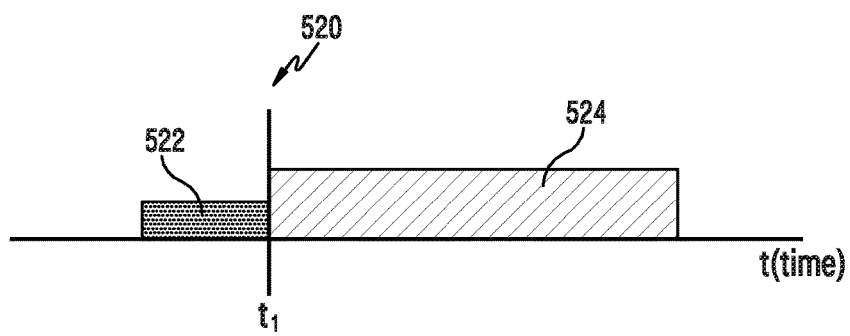
FIG. 5B is a view illustrating an operation of measuring biometric information by an electronic device according to various embodiments of the present disclosure.

FIG. 5B is a view illustrating an operation of measuring biometric information by an electronic device (e.g., the electronic device 101, the processor 120 of the electronic device 101, the electronic device 400, or the processor 500), according to various embodiments of the present disclosure.

Referring to FIG. 5B, the electronic device (e.g., the processor 500) may attempt to measure biometric information according to a period (e.g., about 1 minute) having a selected (or specified) period of time. According to an embodiment, the electronic device (e.g., the processor 500) may operate a first timer that represents a selected (or specified) period of time in order to determine when to attempt to measure biometric information. For example, the electronic device (e.g., the processor 500) may attempt to measure biometric information at every 1 minute by operating the first timer.

According to various embodiments, the electronic device (e.g., the processor 500) may measure the motion of the electronic device in at least one time interval 522 before the operation of the first timer ends (520) (e.g., for about 10 seconds before the operation of the first timer ends), and when the operation of the first timer ends, the electronic device (e.g., the processor 500) may determine whether at least a part of the measured motion satisfies a selected (or specified) reference. For example, the electronic device (e.g., the processor 120 or 500) may measure the average of the motion that is acquired in at least one time interval 522 before the first timer ends, and may determine whether the measured average of the motion is less than, or equal to, a selected (or specified) threshold value.

According to various embodiments, the electronic device (e.g., the processor 500) may operate at least one sensor (e.g., biometric sensor) for measuring biometric information when the measured motion of the electronic device satisfies a selected (or specified) reference.

According to various embodiments, when the measured motion of the electronic device does not satisfy the selected (or specified) reference, the electronic device (e.g., the processor 500) may determine whether the motion of the electronic device is changed to satisfy the selected (or specified) reference for the time 524 (e.g., about 30 seconds) during which a second timer operates. According to an embodiment, the electronic device (e.g., the processor 500) may not measure biometric information when the previously measured motion (e.g., the average of the motion) is maintained at a threshold value or more. According to another embodiment, the electronic device (e.g., the processor 500) may operate at least one sensor (e.g., biometric sensor) for measuring biometric information when the previously measured motion (e.g., the average of the motion) is changed to the threshold value or less. According to yet another embodiment, the electronic device (e.g., the processor 500) may additionally measure the motion of the electronic device for the time 524 during which the second timer operates. According to an embodiment, the electronic device (e.g., the processor 500) may additionally measure the motion of a selected (or specified) time interval (e.g., a time interval that has a magnitude that is the same as, or similar to, that of the time interval 522 in which the average of the motion has been measured) for the time 524 during which the second timer operates, and may determine whether the additionally measured motion satisfies a selected (or specified) reference. For example, the electronic device (e.g., the processor 500) may operate at least one sensor (e.g., biometric sensor) for measuring biometric information when the additionally measured motion satisfies the selected (or specified) reference.

According to various embodiments, the electronic device (e.g., the processor 500) may change the time 524 during which the second timer operates. According to an embodiment, the electronic device (e.g., the processor 500) may increase the time 524 during which the average of the previously measured motion is identified, and may determine whether the measurement of biometric information is possible for the increased time. According to an embodiment, based on the motion (e.g., the strength of the motion) of the electronic device, the electronic device (e.g., the processor 500) may change the time 524 during which the second timer operates. For example, the electronic device (e.g., the processor 500) may increase or decrease the operating time 524 of the second timer based on the previously measure motion (e.g., the average of the motion). For example, when the motion (e.g., the average of the motion) of the electronic device decreases or closely approaches a threshold value, the electronic device (e.g., the processor 500) may increase the operating time 524 of the second timer. For example, when the motion (e.g., the average of the motion) of the electronic device increases or does not closely approach the threshold value, the electronic device (e.g., the processor 500) may decrease the operating time 524 of the second timer.

An electronic device, according to various embodiments, may include: a housing; a fastener coupled to a part of the housing and detachably attached to a part of a user's body; at least one first sensor (e.g., an acceleration sensor, a terrestrial magnetism sensor, a gyro sensor, a proximity sensor, or a combination thereof) configured to detect the motion of the electronic device; at least one second sensor (e.g., a heart rate sensor) configured to detect a change in the user's body; a memory; and a processor electrically connected to the at least one first sensor, the at least one second sensor, and the memory. According to an embodiment, the memory may store instructions that configure the processor to: determine whether the electronic device is worn on (or close to) a part of the user's body using the at least one first sensor; acquire information on the motion of the electronic device using at least a part of the at least one first sensor for a second period of time shortly before and/or immediately after a first period of time selected (or specified) passes from the time when the electronic device is worn on (or close to) a part of the user's body; and activate (operate or trigger) the at least one second sensor based on at least a part of the information on the motion.

According to various embodiments, the determining of whether the electronic device is worn on the user's body part may include determining liveness of the body. According to an embodiment, the determining of the liveness of the body may be performed using at least one of a heart rate sensor, a blood pressure sensor, a body temperature sensor, a skin moisture sensor, an oxygen saturation sensor, a blood glucose sensor, an ECG sensor, an EEG sensor, and an EMG sensor. According to an embodiment, even though the determining of whether the electronic device is worn on (or close to) the user's body part is performed using the at least one first sensor, when it is determined that a signal received from a heart rate sensor is not a signal relating to the body, the electronic device may be determined to not be worn on the user's body part. According to an embodiment, even though the determining of whether the electronic device is worn on (or close to) the user's body part is performed using the at least one first sensor, when it is determined that a signal received from a body temperature sensor is not within a range suitable for the body, the electronic device may be determined to not be worn on the user's body part.

According to various embodiments, the second period of time may be shorter than the first period of time.

According to various embodiments, the at least one first sensor may include a proximity sensor, a gyro sensor, a terrestrial magnetism sensor, or an acceleration sensor.

According to various embodiments, the at least one second sensor may include a biometric sensor. According to an embodiment, the biometric sensor may include at least one of a heart rate sensor, a blood pressure sensor, an ECG sensor, a skin moisture sensor, and an oxygen saturation sensor.

According to various embodiments, the instructions may be set to configure the processor to: acquire additional information on the motion of the electronic device using at least a part of the at least one first sensor for a third period of time, which is shorter than the first period of time, immediately after the second period of time passes; and activate (operate or trigger) the at least one second sensor based on at least a part of the additional information, without activating (operating or triggering) the second sensor when the information on the motion does not satisfy a selected (or specified) condition.

According to various embodiments, at least one of the second period of time and the third period of time may be set to include the time point when the first period of time passes.

According to various embodiments, the second period of time may be set to include the time point when the first period of time passes.

According to various embodiments, when data is not received from the activated (operated or triggered) second sensor within a selected (or specified) time, the instructions may be set to configure the processor to activate (operate or trigger) the second sensor again after the selected (or specified) time passes.

According to various embodiments, the instructions may be set to configure the processor to: acquire additional information on the motion of the electronic device using at least a part of the at least one first sensor for a period of time that is substantially the same as the second period of time before the selected (or specified) time passes; and activate (operate or trigger) the at least one second sensor again based on at least a part of the additional information.

According to various embodiments, the instructions may be set to configure the processor to: acquire data from at least one of the at least one first sensor and the at least one second sensor; and change the first period of time and/or the second period of time and/or the third period of time based on at least a part of the acquired data.

According to various embodiments, the instructions may be set to configure the processor to: acquire data from at least one of the at least one first sensor and the at least one second sensor; and change at least one condition for activating (operating or triggering) the at least one second sensor based on at least a part of the data.

According to various embodiments, the instructions may be set to configure the processor to: acquire data from at least one of the at least one first sensor and the at least one second sensor; and change at least one of a period of time and a sampling rate for activating (operating or triggering) the at least one second sensor based on at least a part of the data.

According to various embodiments, an electronic device may include a memory and a processor electrically connected to the memory. According to an embodiment, the memory may store instructions that configure the processor to: determine whether the electronic device is worn on (or close to) a part of a user's body using at least one first sensor; activate (operate or trigger) at least one second sensor based on at least a part of the motion of the electronic device within a selected (specified) time range at the time when a selected (or specified) period of time passes in a case where the electronic device is worn on (or close to) a part of the user's body; and measure the user's biometric information through the at least one second sensor.

According to various embodiments, the at least one first sensor may include at least one of a proximity sensor, a gyro sensor, a terrestrial magnetism sensor, and an acceleration sensor.

According to various embodiments, the instructions may be set to configure the processor to: acquire additional information on the motion of the electronic device using at least a part of the at least one first sensor for a selected (or specified) time from the time when the period of time passes; and activate (operate or trigger) the at least one second sensor based on at least a part of the additional information, without activating (operating or triggering) the second sensor when at least a part of the motion does not satisfy a selected (or specified) condition.

According to various embodiments, the instructions may be set to configure the processor to change the selected (or specified) time for acquiring the additional information based on data acquired from at least one of the at least one first sensor and the at least one second sensor.

According to various embodiments, the instructions may be set to configure the processor to: accumulate the number of failures when the measurement of the biometric information fails; and deactivate the second sensor when the cumulative number of failures satisfies a selected (or specified) condition.

According to various embodiments, the instructions may be set to configure the processor to acquire data from at least one of the at least one first sensor and the at least one second sensor and activate (operate or trigger) the at least one second sensor based on at least a part of the data.

According to various embodiments, the instructions may be set to configure the processor to acquire data from at least one of the at least one first sensor and the at least one second sensor and change at least one of a period of time or a sampling rate for activating (operating or triggering) the at least one second sensor based on at least a part of the data.

According to various embodiments, an electronic device may include a memory and a processor electrically connected to the memory. According to an embodiment, the memory may be set to configure the processor to: determine whether the electronic device is close to a user's body; acquire information on the motion of the electronic device using at least one first sensor within a selected (or specified) time range from the time when a selected (or specified) period passes in a case where the electronic device is close to the user's body part; and acquire the user's biometric information through at least one second sensor based on at least a part of the information on the motion.

Figure 6:
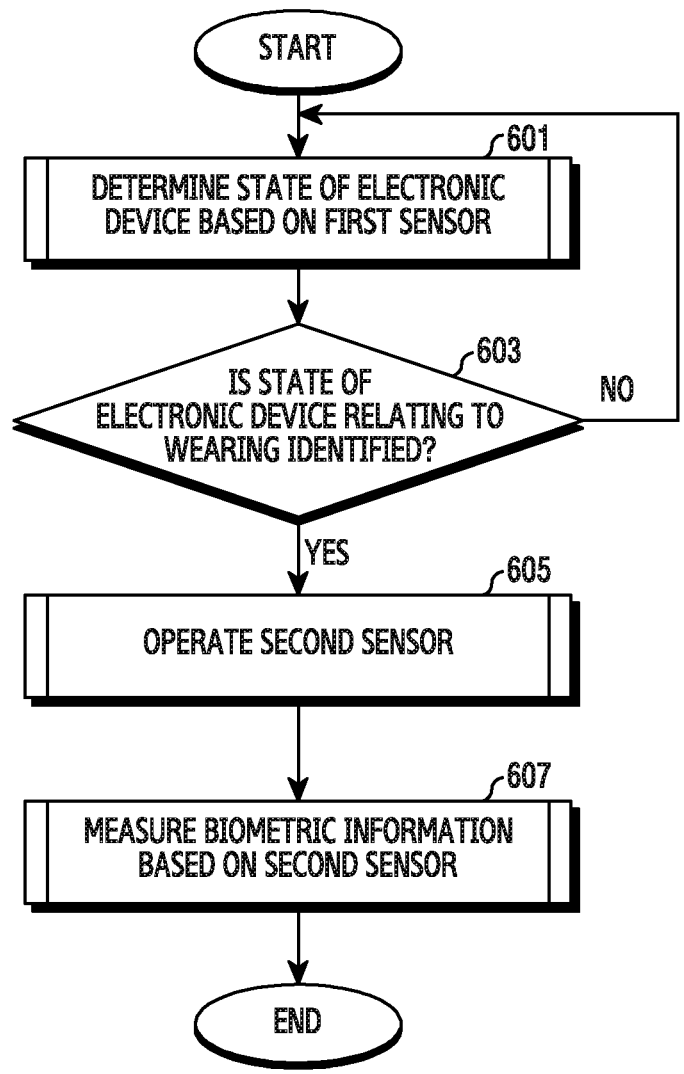
FIG. 6 is a flowchart illustrating a biometric information measurement operation of an electronic device according to various embodiments of the present disclosure.

FIG. 6 is a flowchart illustrating a biometric information measurement operation of an electronic device (e.g., the electronic device 101, the processor 120 of the electronic device 101, the processor 500, or the electronic device 400) according to various embodiments of the present disclosure.

Referring to FIG. 6, in operation 601 the electronic device (e.g., the processor 120 or 500 or the device state determination module 502) may determine the state (e.g., wearing state, proximity state, in-use state, or holding state) of the electronic device based on a first sensor. According to various embodiments, the electronic device (e.g., the processor 120 or 500) may identify the state of the electronic device relating to wearing (or proximity) based on at least one first sensor. According to an embodiment, the state of the electronic device relating to wearing may be a state in which the electronic device makes contact with at least a part of a body, a state in which the electronic device accesses at least a part of a body, etc. According to various embodiments, the first sensor may be constituted by at least one of an acceleration sensor, a terrestrial magnetism sensor, a gyro sensor, a proximity sensor, an atmospheric pressure sensor, and a temperature sensor.

In operation 603, the electronic device (e.g., the processor 120 or 500) may identify the state (e.g., wearing state or non-wearing state) of the electronic device relating to wearing through a state determination operation.

When it is identified in operation 603 that the state of the electronic device relating to wearing does not correspond to a selected (or specified) state (e.g., when the state of the electronic device corresponds to a non-wearing state), the electronic device (e.g., the processor 120 or 500) may perform the operation of determining the state of the electronic device in operation 601.

When it is identified in operation 603 that the state of the electronic device relating to wearing corresponds to the selected (or specified) state (e.g., when the state of the electronic device corresponds to a wearing state), the electronic device (e.g., the processor 120 or 500) may operate at least one second sensor (e.g., the sensor module 470 or the biometric sensor 240I) in operation 605. According to various embodiments, at least one second sensor may be a sensor for measuring biometric information, and may measure at least one of a blood pressure, a heart rate, an ECG, skin moisture, saturation of peripheral oxygen, a body temperature, blood glucose, an EEG, an EMG, and the like. For example, the second sensor may be disposed on one surface of the electronic device so as to be brought into contact with a body.

According to various embodiments, the electronic device may operate at least one second sensor based on at least one of when a selected (or specified) period of time has elapsed, when the motion of the electronic device that is acquired using at least a part of at least one first sensor satisfies a selected (or specified) reference, and when a selected (or specified) time arrives. According to an embodiment, when the state of the electronic device is determined to be a wearing state, the electronic device may operate a first timer that represents a selected (or specified) period of time and may operate at least one second sensor when the first timer ends. According to an embodiment, when the state of the electronic device is determined to be a wearing state, the electronic device may identify the motion of the electronic device and may operate at least one second sensor when the motion satisfies a selected (or specified) reference. According to an embodiment, when the state of the electronic device is determined to be a wearing state, the electronic device may identify whether a selected (or specified) time (e.g., about 6:11 in a case where a wearing determination time is about 6:10) arrives and may operate at least one second sensor.

In operation 607, the electronic device (e.g., the processor 120 or 500 or the measurement module 506) may measure biometric information based on the second sensor. According to various embodiments, the electronic device (e.g., the processor 120 or 500) may output the biometric information measured based on the second sensor on a screen thereof. According to an embodiment, the electronic device (e.g., the processor 120 or 500) may provide a health care function (e.g., providing a heart rate or a work rate) based on the measured biometric information.

Figure 7:
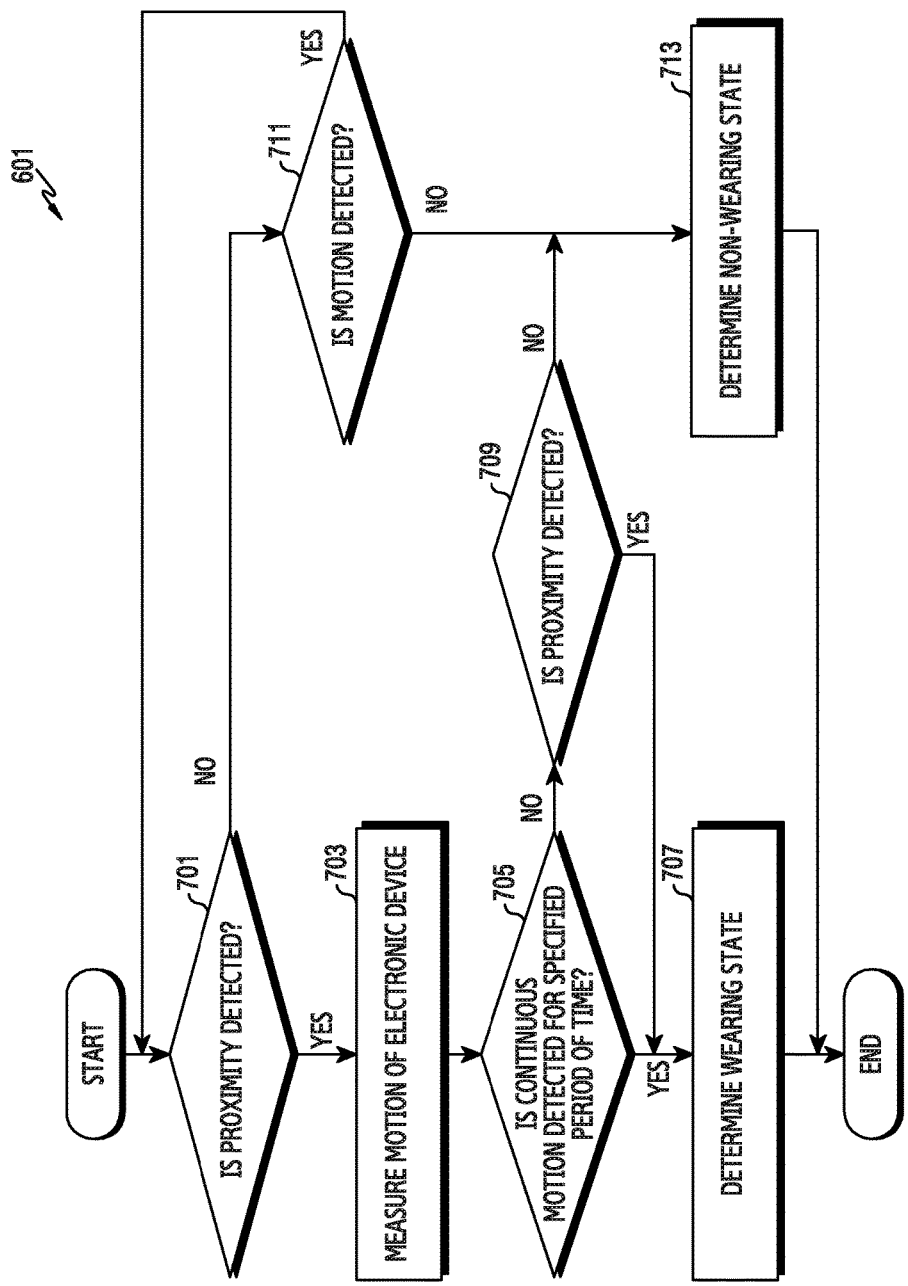
FIG. 7 is a flowchart illustrating a performance procedure of a method of determining the state of an electronic device according to various embodiments of the present disclosure.

FIG. 7 is a flowchart illustrating a performance procedure of a method of determining the state of an electronic device (e.g., the electronic device 101, the processor 120 of the electronic device 101, the processor 500, or the electronic device 400) according to various embodiments of the present disclosure.

Referring to FIG. 7, the performance procedure of the state determination method may be a detailed operation for the operation 601 illustrated in FIG. 6.

In operation 701, the electronic device (e.g., the processor 120 or 500) may identify whether the proximity of an external object (e.g., a user) to the electronic device is detected based on at least one first sensor (e.g., proximity sensor). According to various embodiments, the proximity may be associated with a state in which the electronic device is close to a body, a state in which the electronic device makes contact with a body, etc. For example, the electronic device (e.g., the processor 120 or 500) may determine whether the electronic device is close to a body based on information acquired through the proximity sensor, which is the first sensor.

When the proximity of the user (e.g., body) to the electronic device is detected in operation 701, the electronic device (e.g., the processor 120 or 500) may measure the motion of the electronic device based on at least one first sensor (e.g., an acceleration sensor, a terrestrial magnetism sensor, or a gyro sensor) in operation 703. According to various embodiments, the motion may be associated with the motion of the electronic device or user. According to an embodiment, the electronic device (e.g., the processor 120 or 500) may measure the motion based on information acquired through at least one of an acceleration sensor, a terrestrial magnetism sensor, and a gyro sensor in response to the detection of the proximity.

In operation 705, the electronic device (e.g., the processor 120 or 500) may identify whether a motion that satisfies a selected (or specified) condition is detected. According to various embodiments, the electronic device (e.g., the processor 120 or 500) may identify whether a continuous motion is detected for a selected (or specified) period of time while the electronic device is close to a body. For example, when the continuous motion is detected for the selected (or specified) period of time, the electronic device (e.g., the processor 120 or 500) may determine that the motion that satisfies the condition is detected.

When the motion that satisfies the selected (or specified) condition is detected in operation 705, the electronic device (e.g., the processor 120 or 500) may determine the state of the electronic device to be a state relating to wearing in operation 707.

When the motion that satisfies the selected (or specified) condition is not detected in operation 705, the electronic device (e.g., the processor 120 or 500) may identify whether the proximity of a body to the electronic device is detected based on at least one first sensor (e.g., a proximity sensor) in operation 709. For example, the electronic device may determine whether the electronic device is close to the body based on information acquired through the proximity sensor, which is the first sensor.

When the proximity of the body to the electronic device is detected in operation 709, the electronic device (e.g., the processor 120 or 500) may determine the state of the electronic device to be a state relating to wearing (e.g., wearing state) in operation 707. In one embodiment, when the electronic device makes contact with, or is close to, a body in a motionless state (e.g., sleep state), the electronic device (e.g., the processor 120 or 500) may determine the state of the electronic device to be a state relating to wearing.

When the proximity of a body to the electronic device is not detected in operation 709, the electronic device (e.g., the processor 120 or 500) may determine the state of the electronic device to be a state not relating to wearing (e.g., non-wearing state) in operation 713.

When the proximity of an external object to the electronic device is not detected in operation 701, the electronic device (e.g., the processor 120 or 500) may identify whether the motion of the electronic device is detected in operation 711. According to various embodiments, in the state in which no proximity is detected, the electronic device (e.g., the processor 120 or 500) may determine whether to perform the operation of determining the detection of proximity again based on the motion of the electronic device. For example, although no proximity is detected, the electronic device (e.g., the processor 120 or 500) may determine that proximity is likely to be detected when the motion of the electronic device is detected.

When the motion of the electronic device is detected in operation 711, the electronic device (e.g., the processor 120 or 500) may determine whether the electronic device is close to a body based on at least one first sensor in operation 701.

When the motion of the electronic device is not detected in operation 711, the electronic device (e.g., the processor 120 or 500) may determine the state of the electronic device to be a state not relating to wearing (e.g., non-wearing state) in operation 713. For example, the electronic device (e.g., the processor 120 or 500) may determine that the electronic device is unlikely to access a body and may determine the state of the electronic device to be a state not relating to wearing.

According to various embodiments, at least one of the operations 701 to 713 may be omitted. For example, in operation 701, the electronic device (e.g., the processor 120 or 500) may identify whether the proximity of a user to the electronic device is detected. When the proximity of the user to the electronic device is detected, the electronic device (e.g., the processor 120 or 500) may determine the state of the electronic device to be a state relating to wearing (e.g., wearing state) in operation 707. Furthermore, when the proximity of the user to the electronic device is not detected, the electronic device (e.g., the processor 120 or 500) may determine the state of the electronic device to be a state not relating to wearing (e.g., non-wearing state) in operation 713.

According to various embodiments, in operation 703, the electronic device (e.g., the processor 120 or 500) may measure the motion of the electronic device. In operation 705, the electronic device (e.g., the processor 120 or 500) may identify whether the motion (e.g., continuous motion) is detected for a specified (or selected) period of time. When the motion (continuous motion) is detected for the selected (or specified) period of time, the electronic device (e.g., the processor 120 or 500) may determine the state of the electronic device to be a state (e.g., wearing state) relating to wearing (or a state in which the user holds or uses the electronic device) in operation 707. When the continuous motion is not detected for the selected (or specified) period of time, the electronic device (e.g., the processor 120 or 500) may determine the state of the electronic device to be a state (non-wearing state) not relating to wearing (or a state in which the user does not hold or use the electronic device) in operation 713.

Figure 8:
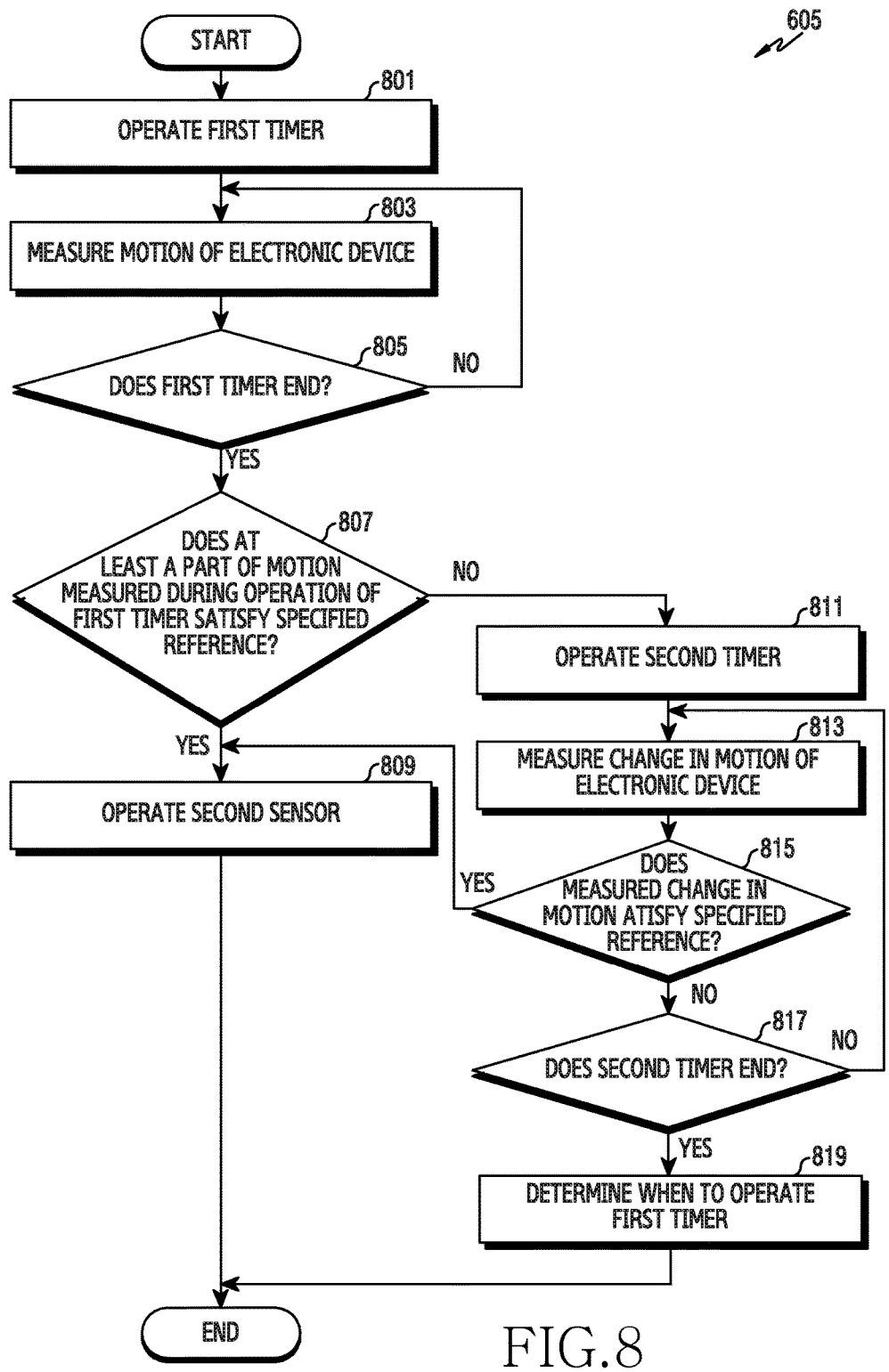
FIG. 8 is a flowchart illustrating the performance procedure of a method of operating a sensor by an electronic device according to various embodiments of the present disclosure.

FIG. 8 is a flowchart illustrating the performance procedure of a method of operating a second sensor by an electronic device (e.g., the electronic device 101, the processor 120 of the electronic device 101, the processor 500, or the electronic device 400) according to various embodiments of the present disclosure.

Referring to FIG. 8, the performance procedure of the method of operating the second sensor may be a detailed operation for the operation 605 illustrated in FIG. 6.

In operation 801, the electronic device (e.g., the processor 120 or 500) may operate a first timer that operates for a selected (or specified) period of time. According to various embodiments, the electronic device (e.g., the processor 120 or 500) may attempt to measure biometric information based on the operation of the first timer. According to an embodiment, the first timer may be time on the basis of which when to attempt to measure biometric information is determined. For example, the first timer may operate in about 1-minute periods.

In operation 803, the electronic device (e.g., the processor 120 or 500) may measure the motion of the electronic device in response to the operation of the timer. According to an embodiment, the electronic device (e.g., the processor 120 or 500) may detect the motion of the electronic device based on at least one first sensor (e.g., an acceleration sensor or a gyro sensor). According to various embodiments, based on the operation of the first timer, the electronic device (e.g., the processor 120 or 500) may measure the motion of the electronic device until the first timer ends.

In operation 805, the electronic device (e.g., the processor 120 or 500) may identify whether the first timer ends. The time when the first timer ends may be, for example, the time when whether to perform an operation of measuring biometric information is determined. The operation of measuring the biometric information may be, for example, an operation of driving at least one second sensor for measuring biometric information.

When the first timer does not end in operation 805, the electronic device (e.g., the processor 120 or 500) may measure the motion of the electronic device in operation 803. For example, the electronic device (e.g., the processor 120 or 500) may measure the motion of the electronic device until the first timer ends.

When the first timer ends in operation 805, the electronic device (e.g., the processor 120 or 500) may determine whether the motion of the electronic device, which is measured during the operation of the first timer, satisfies a selected (or specified) reference in operation 807. According to an embodiment, the electronic device (e.g., the processor 120 or 500) may determine whether a motion by which biometric information can be accurately measured is generated. According to various embodiments, the electronic device (e.g., the processor 120 or 500) may determine whether at least a part of the motion measured during the operation of the first timer satisfies a selected (or specified) reference. According to an embodiment, the electronic device (e.g., the processor 120 or 500) may measure the average of the motion measured during the operation of the first timer and may determine whether the measured average of the motion satisfies a selected (or specified) reference. According to another embodiment, the electronic device (e.g., the processor 120 or 500) may measure the average of the motion acquired in at least one time interval before the first timer ends and may determine whether the measured average of the motion satisfies a selected (or specified) reference. According to various embodiments, the situation in which the selected (or specified) condition is satisfied may be a situation in which the motion of the electronic device that is less than, or equal to, a selected (or specified) threshold value is measured. For example, the situation in which the motion of the electronic device that is less than, or equal to, the selected (or specified) threshold value is measured may be a state in which the motion of the electronic device is not generated, or a state in which the motion of the electronic device is so small that it is recognized as not being generated.

When the motion of the electronic device, which is measured during the operation of the first timer, satisfies the selected (or specified) reference in operation 807, the electronic device (e.g., the processor 120 or 500) may operate at least one second sensor for measuring biometric information in operation 809.

When the motion of the electronic device, which is measured during the operation of the first timer, does not satisfy the selected (or specified) reference in operation 807, the electronic device (e.g., the processor 120 or 500) may operate a second timer that operates for a selected (or specified) period of time in operation 811. According to an embodiment, the electronic device (e.g., the processor 120 or 500) may operate the second timer in order to determine whether the measured motion of the electronic device that does not satisfy the reference is changed to satisfy the selected (or specified) reference. The operating time of the second timer may be shorter than that of the first timer. For example, the electronic device (e.g., the processor 120 or 500) may identify whether the motion of the electronic device changes until the next period for the measurement of biometric information arrives.

In operation 813, the electronic device (e.g., the processor 120 or 500) may measure a change in the motion of the electronic device.

In operation 815, the electronic device (e.g., the processor 120 or 500) may identify whether the measured change in the motion satisfies a selected (or specified) reference. According to an embodiment, the electronic device (e.g., the processor 120 or 500) may determine whether the measured motion (e.g., the motion of the electronic device that does not satisfy the reference) is changed into a motion by which biometric information can be accurately measured. For example, the electronic device (e.g., the processor 120 or 500) may identify whether the average value of the motion that is measured when the first timer ends is changed to a selected (or specified) threshold value or less.

When the change in the motion satisfies the selected (or specified) reference in operation 815, the electronic device (e.g., the processor 120 or 500) may measure biometric information. For example, the electronic device (e.g., the processor 120 or 500) may operate at least one second sensor for measuring biometric information in operation 809.

When the change in the motion does not satisfy the selected (or specified) reference in operation 815, the electronic device (e.g., the processor 120 or 500) may identify whether the second time ends in operation 817.

When the second timer does not end in operation 817, the electronic device (e.g., the processor 120 or 500) may identify whether the change in the motion of the electronic device (e.g., the processor 120 or 500) satisfies the selected (or specified) reference again while the second timer operates. For example, the electronic device (e.g., the processor 120 or 500) may measure a change in the motion of the electronic device in operation 813.

When the second timer ends in operation 817, the electronic device (e.g., the processor 120 or 500) may determine when to operate the first timer in operation 819. For example, the electronic device (e.g., the processor 120 or 500) may determine the state of the electronic device relating to wearing. In another example, as the electronic device (e.g., the processor 120 or 500) determines the state (e.g., wearing state) of the electronic device relating to wearing, the electronic device may omit the operation of determining the state of the electronic device and may operate the first timer.

According to various embodiments, at least one of the operations 801 to 819 may be omitted. When the motion of the electronic device 101, which is measured during the operation of the first timer, satisfies the selected (or specified) reference in operation 807, the electronic device 101 (e.g., the processor 120 or 500) may operate at least one second sensor for measuring biometric information in operation 809. When the motion of the electronic device 101, which is measured during the operation of the first timer, does not satisfy the selected (or specified) reference in operation 807, the electronic device (e.g., the processor 120 or 500) may determine when to operate the first timer in operation 819. For example, the electronic device (e.g., the processor 120 or 500) may determine the state of the electronic device relating to wearing. In another example, as the electronic device (e.g., the processor 120 or 500) determines the state (e.g., wearing state) of the electronic device relating to wearing, the electronic device may omit the operation of determining the state of the electronic device and may operate the first timer.

Figure 9:
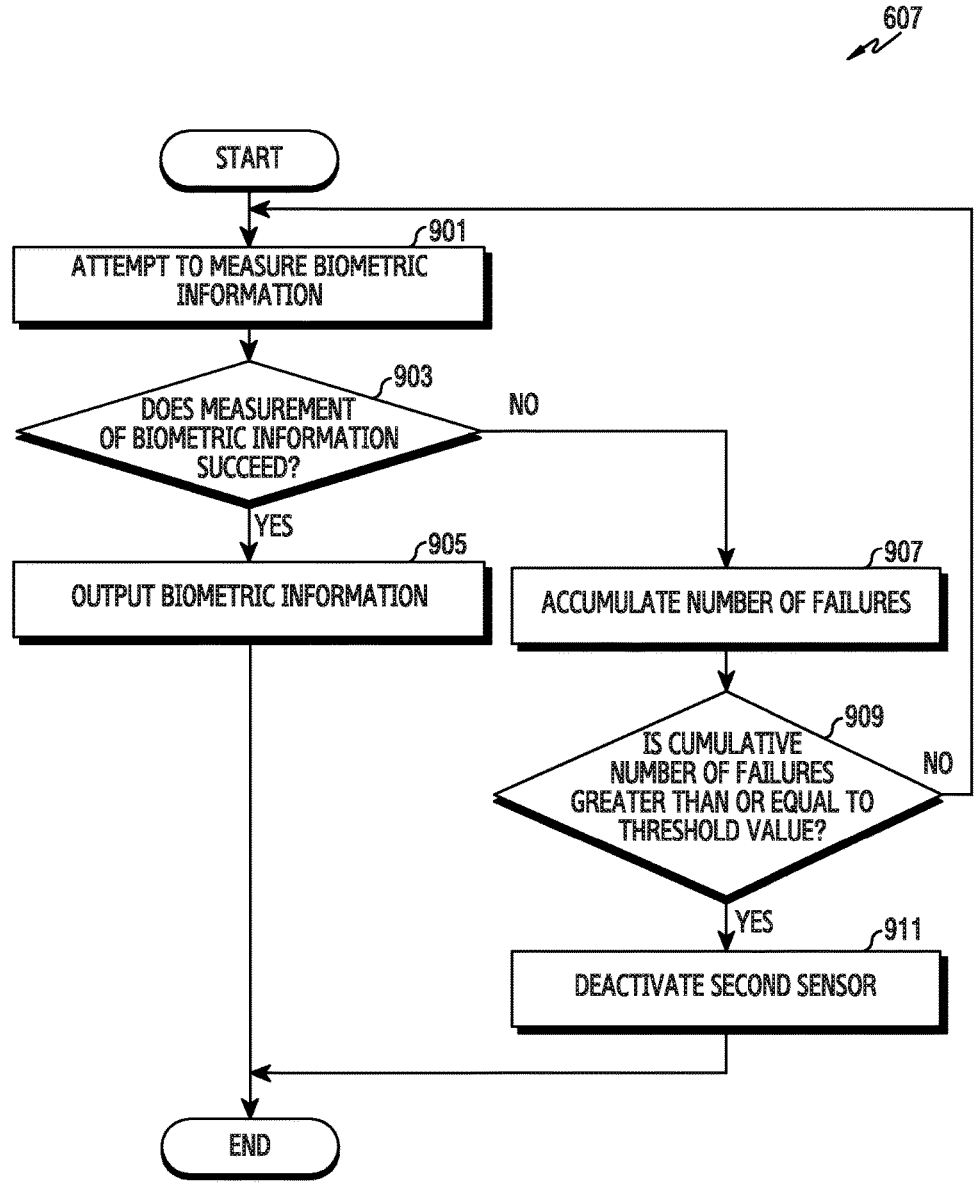
FIG. 9 is a flowchart illustrating the performance procedure of a method of measuring biometric information by an electronic device according to various embodiments of the present disclosure.

FIG. 9 is a flowchart illustrating the performance procedure of a method of measuring biometric information by an electronic device (e.g., the electronic device 101, the processor 120 of the electronic device 101, the processor 500, or the electronic device 400) according to various embodiments of the present disclosure.

Referring to FIG. 9, the performance procedure of the method of measuring biometric information may be a detailed operation for the operation 607 illustrated in FIG. 6.

In operation 901, the electronic device (e.g., the processor 120 or 500) may attempt to measure biometric information. According to various embodiments, the measurement of biometric information may be performed by operating at least one second sensor. According to various embodiments, the second sensor may include a light emitting part that emits light and a light receiving part that receives the light of the light emitting part, and the electronic device (e.g., the processor 120 or 500) may measure biometric information based on a signal output from the second sensor. According to an embodiment, the electronic device (e.g., the processor 120 or 500) may measure biometric information (e.g., a heart rate) based on the amount of light output through at least one second sensor that makes contact with at least a part of a body. For example, slightly dark light may be received for a systolic period of the heart cycle due to a large amount of blood in a body part, and bright light may be received for a diastolic period of the heart cycle due to a relatively small amount of blood in the body part. The electronic device (e.g., the processor 120 or 500) may measure heart rate information based on the amount of light.

In operation 903, the electronic device (e.g., the processor 120 or 500) may identify whether the biometric information is successfully measured. According to an embodiment, the electronic device (e.g., the processor 120 or 500) may identify whether a normal measurement result is obtained. According to an embodiment, the electronic device (e.g., the processor 120 or 500) may identify whether a normal measurement result is obtained based on the time devoted to measuring the biometric information. For example, when a measurement result is not obtained within a selected (or specified) time after the measurement of the biometric information starts, the electronic device (e.g., the processor 120 or 500) may determine that the measurement of the biometric information has failed. According to another embodiment, the electronic device (e.g., the processor 120 or 500) may identify whether a normal measurement result is obtained based on the motion of the electronic device. For example, when a motion that does not satisfy a selected (or specified) condition is detected after the measurement of the biometric information starts, the electronic device (e.g., the processor 120 or 500) may determine that the measurement of the biometric information has failed.

When the biometric information is successfully measured in operation 903, the electronic device (e.g., the processor 120 or 500) may output the measured biometric information in operation 905. According to an embodiment, the electronic device (e.g., the processor 120 or 500) may display the measurement result on a display thereof (e.g., a screen) based on the second sensor. According to another embodiment, the electronic device (e.g., the processor 120 or 500) may provide a health care function (e.g., providing whether a heart rate is normal or not) based on the measurement result.

When no biometric information is measured in operation 903, the electronic device (e.g., the processor 120 or 500) may accumulate the number of failures in operation 907. According to an embodiment, the electronic device (e.g., the processor 120 or 500) may accumulate the number of failures every time a normal result is not obtained after the electronic device attempts to measure biometric information. For example, when a normal measurement result on biometric information is not obtained once, the electronic device (e.g., the processor 120 or 500) may determine the number of failures to be one in operation 907. Furthermore, when a normal measurement result on biometric information is not obtained three times, the electronic device (e.g., the processor 120 or 500) may determine the number of failures to be three in operation 907.

In operation 909, the electronic device (e.g., the processor 120 or 500) may identify the cumulative number of failures. According to an embodiment, the electronic device (e.g., the processor 120 or 500) may identify whether the cumulative number of failures is greater than, or equal to, a threshold value (e.g., about three times). According to various embodiments, when the cumulative number of failures is greater than, or equal to, the threshold value, the electronic device may determine that the measurement has continually failed so that it is impossible to measure biometric information.

When it is identified in operation 909 that the cumulative number of failures is smaller than the threshold value, the electronic device (e.g., the processor 120 or 500) may attempt to measure biometric information again. According to an embodiment, the electronic device (e.g., the processor 120 or 500) may perform an operation associated with operation 901 again. According to another embodiment, the electronic device (e.g., the processor 120 or 500) may measure biometric information based on the motion of the electronic device. For example, the electronic device (e.g., the processor 120 or 500) may perform at least one of the operations 801 to 819.

When it is identified in operation 909 that the cumulative number of failures is greater than, or equal to, the threshold value, the electronic device (e.g., the processor 120 or 500) may deactivate at least one second sensor. According to an embodiment, the electronic device (e.g., the processor 120 or 500) may determine that it is impossible to measure biometric information, and may stop the operation of the second sensor accordingly in operation 911.

According to various embodiments, at least one of the operations 901 to 911 may be omitted. For example, the operations 907 to 911 may be omitted. Accordingly, in a case where the measurement of biometric information fails in operation 903, the electronic device (e.g., the processor 120 or 500) may perform operation 901 again.

Figure 10:
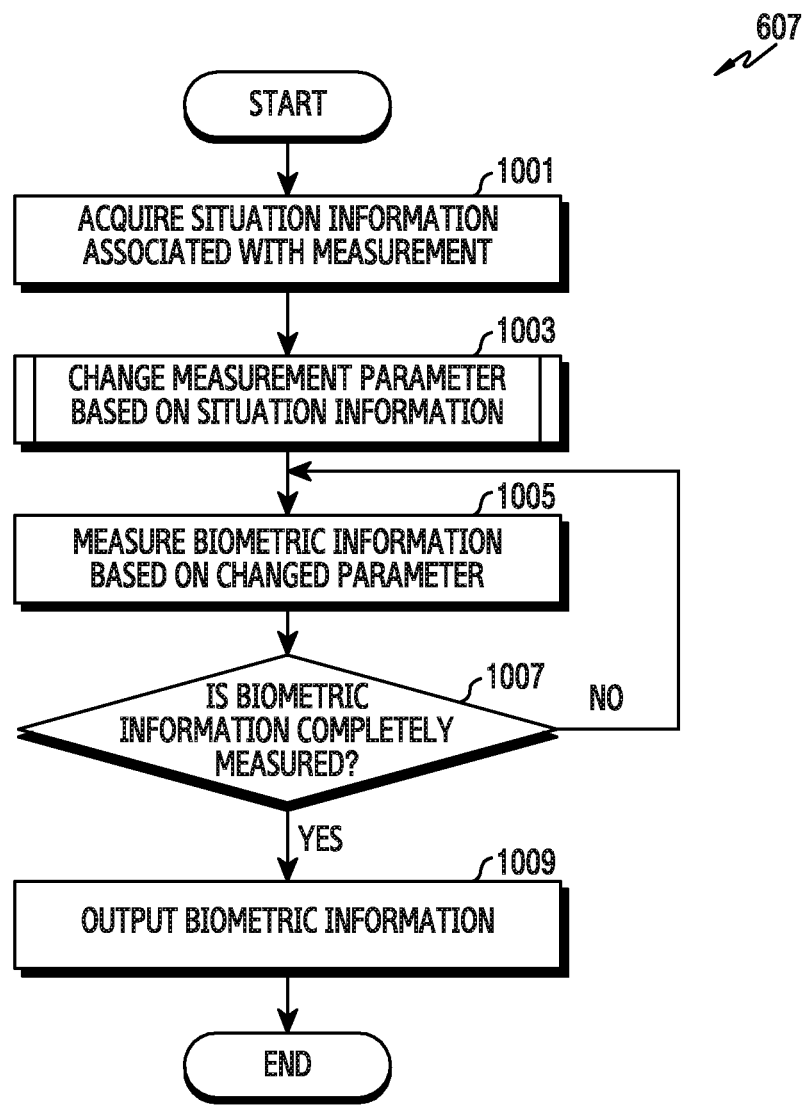
FIG. 10 is a flowchart illustrating the performance procedure of a method of measuring biometric information by an electronic device according to various embodiments of the present disclosure.

FIG. 10 is a flowchart illustrating the performance procedure of a method of measuring biometric information by an electronic device (e.g., the electronic device 101, the processor 120 of the electronic device 101, the processor 500, or the electronic device 400) according to various embodiments of the present disclosure.

Referring to FIG. 10, the performance procedure of the method of measuring biometric information may be a detailed operation for the operation 607 illustrated in FIG. 6.

In operation 1001, the electronic device (e.g., the processor 120 or 500) may acquire situation information associated with a measurement. According to various embodiments, the electronic device (e.g., the processor 120 or 500) may acquire the situation information based on at least one first sensor and/or at least one second sensor. According to an embodiment, the situation information may include the motion of the electronic device or a body while biometric information is being measured, the physical characteristic of an object to be measured, the state of the object to be measured, a measurement quality, a measurement result, or the like.

In operation 1003, the electronic device (e.g., the processor 120 or 500) may change a measurement parameter based on the situation information. For example, the measurement parameter that is changed based on the situation information may be defined as listed in Table 1 below. However, various embodiments of the present disclosure are not limited to Table 1. For example, in a case where the situation information is 'measurement quality,' the parameter to be changed may be 'timer period.' Furthermore, in a case where the situation information is 'physical characteristic,' the parameter to be changed may be 'sampling rate.'

TABLE 1

| Situation information | Parameter to be changed |
| --- | --- |
| Measurement quality | Measurement time (light-emitting time) |
| Motion | Sampling rate |
| Measurement result | Measurement trigger |
| Physical condition | Timer period |
| User's state | Condition for determining motion |

According to an embodiment, the electronic device (e.g., the processor 120 or 500) may reduce power consumption that is generated when biometric information is measured by changing the measurement parameter based on the situation information. According to an embodiment, the electronic device (e.g., the processor 120 or 500) may increase the accuracy of measurement when measuring biometric information by changing the measurement parameter based on the situation information.

For example, the electronic device (e.g., the processor 120 or 500) may determine that it is useless to measure biometric information in a state in which a measurement quality is not good. Accordingly, the electronic device (e.g., the processor 120 or 500) may decrease the light-emitting time of the second sensor in order to reduce power consumption. In another example, when the motion strength of the electronic device that cannot be normally measured is detected while biometric information is being measured, the electronic device (e.g., the processor 120 or 500) may stop the measurement operation in order to reduce power consumption. In yet another example, when the electronic device (e.g., the processor 120 or 500) continually fails to measure biometric information due to the motion thereof, the electronic device may omit the measurement operation until the motion is not generated in order to reduce power consumption. In yet another example, when it is determined that the strength of a motion while biometric information is being measured can be corrected, the electronic device (e.g., the processor 120 or 500) may increase a measurement sampling rate during the measurement operation in order to enhance the accuracy of measurement. In yet another example, when the electronic device (e.g., the processor 120 or 500) detects a physical characteristic (e.g., a dark skin color) of an object to be measured that uses an amount of light more than a reference value, which is emitted from the second sensor, the electronic device may change the measurement period in order to decrease the number of times that biometric information is measured, thereby reducing power consumption. In yet another example, in the case of a user in a motionless state (e.g., a sleep state), the electronic device (e.g., the processor 120 or 500) may omit an operation of determining the motion of the electronic device in order to reduce power consumption.

In operation 1005, the electronic device (e.g., the processor 120 or 500) may measure biometric information based on the changed parameter.

In operation 1007, the electronic device (e.g., the processor 120 or 500) may identify whether the biometric information is completely measured. According to an embodiment, the electronic device (e.g., the processor 120 or 500) may identify whether the biometric information measurement result is successfully obtained.

When the measurement of the biometric information is not completed in operation 1007, the electronic device (e.g., the processor 120 or 500) may measure biometric information. According to an embodiment, the electronic device (e.g., the processor 120 or 500) may measure the biometric information based on the changed parameter in operation 1005.

When the measurement of biometric information is completed in operation 1007, the electronic device (e.g., the processor 120 or 500) may output the measured biometric information in operation 1009. For example, the electronic device (e.g., the processor 120 or 500) may output the measured biometric information through a display or a speaker.

According to various embodiments, at least one of the operations 1001 to 1009 may be omitted. For example, operation 1009 may be omitted.

Figure 11:
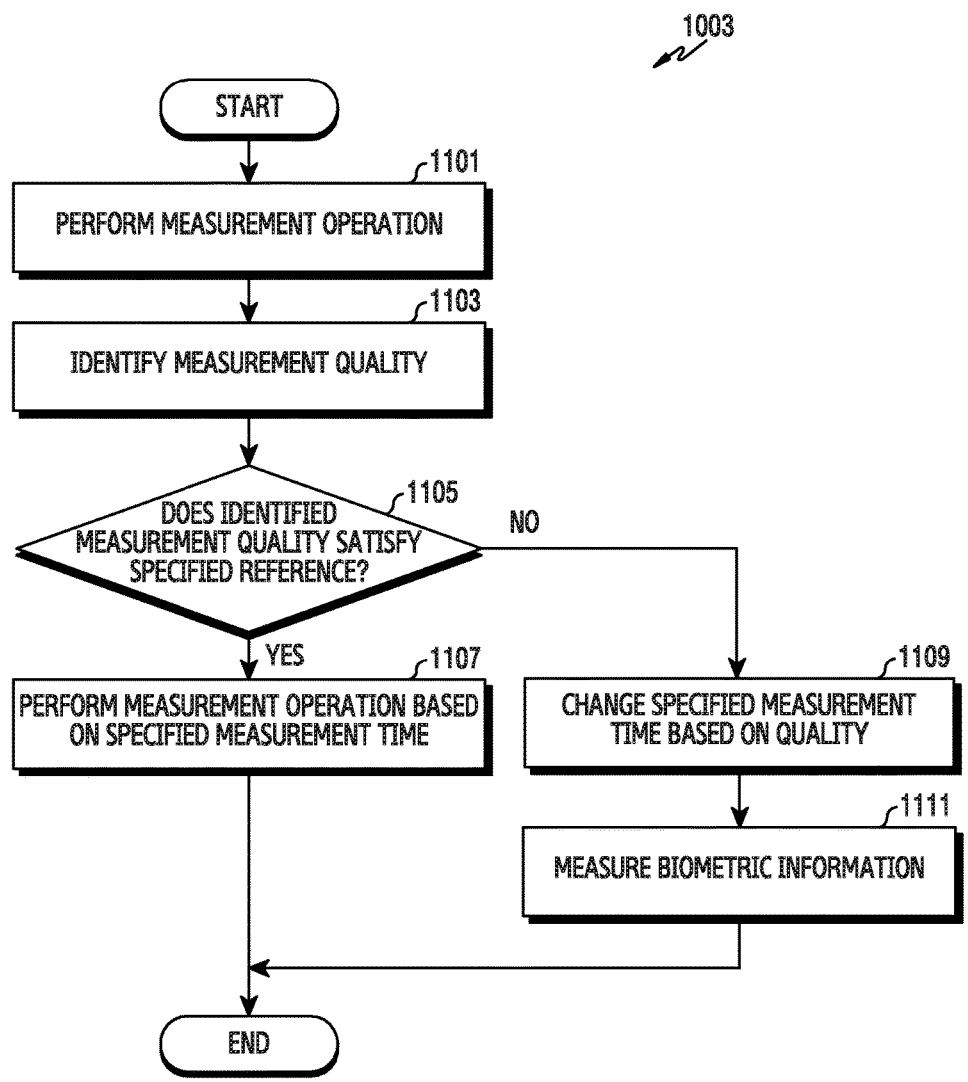
FIG. 11 is a flowchart illustrating the performance procedure of a method of changing a measurement parameter by an electronic device according to various embodiments of the present disclosure.

FIG. 11 is a flowchart illustrating the performance procedure of a method of changing a measurement parameter by an electronic device (e.g., the electronic device 101, the processor 120 of the electronic device 101, the processor 500, or the electronic device 400) according to various embodiments of the present disclosure.

Referring to FIG. 11, the performance procedure of the method of changing a measurement parameter may be a detailed operation for the operation 1003 illustrated in FIG. 10.

According to an embodiment, the electronic device (e.g., the processor 120 or 500) may determine that it is useless to measure biometric information in a state in which a measurement quality is not good and may decrease the light-emitting time of a second sensor in order to reduce power consumption.

In operation 1101, the electronic device (e.g., the processor 120 or 500) may measure biometric information. According to an embodiment, the electronic device (e.g., the processor 120 or 500) may operate at least one second sensor to emit light for a selected (or specified) period of time and may acquire a signal output from the second sensor.

In operation 1103, the electronic device (e.g., the processor 120 or 500) may identify the measurement quality. According to an embodiment, the measurement quality may be the quality of a signal output from the second sensor. For example, the electronic device (e.g., the processor 120 or 500) may acquire a signal to noise ratio for the signal output from the second sensor as the measurement quality.

In operation 1105, the electronic device (e.g., the processor 120 or 500) may identify whether the measurement quality satisfies a selected (or specified) reference. According to an embodiment, the measurement quality may not satisfy the selected (or specified) reference, which may mean that a signal used for measuring biometric information is not acquired. For example, the measurement quality that fails to satisfy the selected (or specified) reference may indicate that a normal measurement result is not obtained. In another example, the measurement quality that fails to satisfy the selected (or specified) reference may indicate that a measurement result is not obtained for a selected (or specified) measurement time.

When the measurement quality satisfies the selected (or specified) reference in operation 1105, the electronic device (e.g., the processor 120 or 500) may measure biometric information based on a selected (or specified) measurement time in operation 1107. According to various embodiments, the measurement time may be associated with the light-emitting time of the second sensor. According to an embodiment, when the measurement quality satisfies the selected (or specified) reference, the electronic device (e.g., the processor 120 or 500) may acquire biometric information by emitting light through the second sensor for the selected (or specified) time (e.g., about 10 seconds) every time a biometric information measurement period (e.g., about 1-minute period) arrives.

When the measurement quality does not satisfy the selected (or specified) reference in operation 1105, the electronic device (e.g., the processor 120 or 500) may change the measurement time selected (or specified) based on the quality in operation 1109.

According to various embodiments, the electronic device (e.g., the processor 120 or 500) may change the measurement time in order to reduce power consumption. According to an embodiment, the electronic device (e.g., the processor 120 or 500) may shorten the measurement time in order to reduce power consumption when the measurement result on the biometric information is not obtained for the selected (or specified) measurement time.

According to various embodiments, the electronic device (e.g., the processor 120 or 500) may change the measurement time in order to enhance the accuracy of the measurement result. According to an embodiment, when the measurement result on the biometric information is not obtained for the selected (or specified) measurement time, the electronic device (e.g., the processor 120 or 500) may increase the measurement time in order to sufficiently ensure the information used for measuring the biometric information.

In operation 1111, the electronic device (e.g., the processor 120 or 500) may measure biometric information based on the changed measurement time.

According to various embodiments, at least one of the operations 1101 to 1111 may be omitted.

Figure 12:
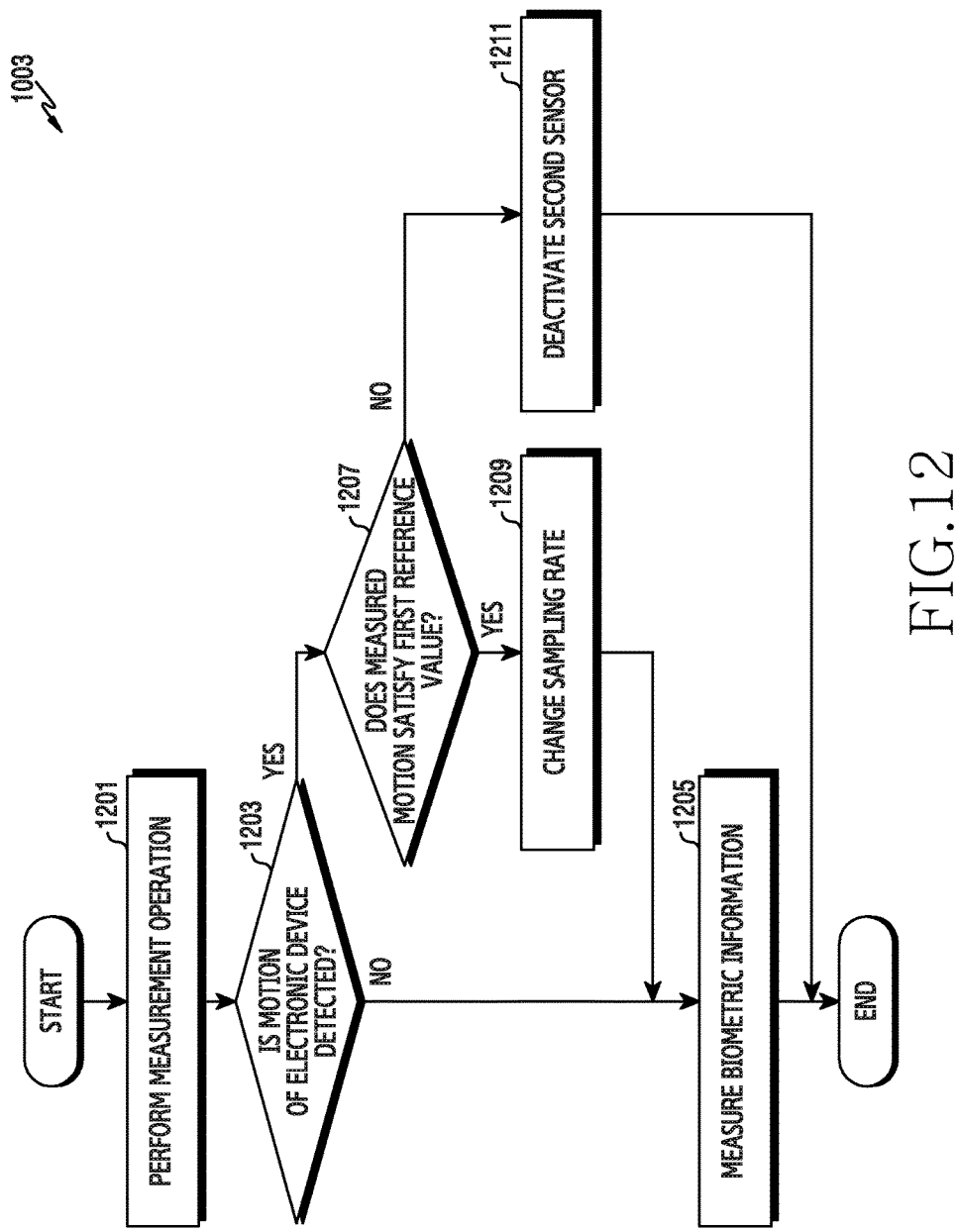
FIG. 12 is a flowchart illustrating the performance procedure of a method of changing a measurement parameter by an electronic device according to various embodiments of the present disclosure.

FIG. 12 is a flowchart illustrating the performance procedure of a method of changing a measurement parameter by an electronic device (e.g., the electronic device 101, the processor 120 of the electronic device 101, the processor 500, or the electronic device 400) according to various embodiments of the present disclosure.

Referring to FIG. 12, the performance procedure of the method of changing a measurement parameter may be a detailed operation for the operation 1003 illustrated in FIG. 10.

In operation 1201, the electronic device (e.g., the processor 120 or 500) may measure biometric information. According to an embodiment, the electronic device (e.g., the processor 120 or 500) may operate at least one second sensor to emit light for a selected (or specified) period of time and may acquire a signal output from the second sensor.

In operation 1203, the electronic device (e.g., the processor 120 or 500) may identify whether the motion of the electronic device is detected while the biometric information is being measured. According to various embodiments, the electronic device (e.g., the processor 120 or 500) may measure the motion of the electronic device based on at least one first sensor.

When the motion of the electronic device is not detected in operation 1203, the electronic device (e.g., the processor 120 or 500) may measure biometric information in operation 1205. According to various embodiments, the electronic device (e.g., the processor 120 or 500) may acquire information output from the second sensor based on a selected (or specified) sampling rate.

When the motion of the electronic device is detected in operation 1203, the electronic device (e.g., the processor 120 or 500) may identify whether the measured motion satisfies a selected (or specified) reference value in operation 1207.

According to an embodiment, the electronic device (e.g., the processor 120 or 500) may identify whether a low motion strength that does not affect the measurement result is detected. For example, the electronic device (e.g., the processor 120 or 500) may determine the motion strength that does not affect the measurement result to be a motion that satisfies the reference value. According to an embodiment, the electronic device (e.g., the processor 120 or 500) may identify whether a motion strength that may affect the measurement result, but can be corrected, is detected. For example, the electronic device (e.g., the processor 120 or 500) may determine a value larger than the motion strength, which does not affect the measurement result, by a predetermined value or more to be a reference value.

When the motion is identified to satisfy the reference value in operation 1207, the electronic device (e.g., the processor 120 or 500) may change the sampling rate of a signal output from the second sensor in operation 1209. According to an embodiment, the electronic device (e.g., the processor 120 or 500) may increase a signal output from the second sensor by increasing the sampling rate in order to correct the noise according to the motion thereof.

When it is identified in operation 1207 that the motion does not satisfy the reference value, the electronic device (e.g., the processor 120 or 500) may deactivate the second sensor in operation 1211. According to an embodiment, the electronic device (e.g., the processor 120 or 500) may determine that it is impossible to correct the noise according to the motion, and may accordingly stop measuring the biometric information.

According to various embodiments, at least one of the operations 1201 to 1211 may be omitted. For example, the operations 1207 and 1211 may be omitted. In this case, when the motion of the electronic device is detected in operation 1203, the electronic device may change the sampling rate in operation 1209. The electronic device may measure biometric information according to the changed sampling rate in operation 1205.

Figure 13:
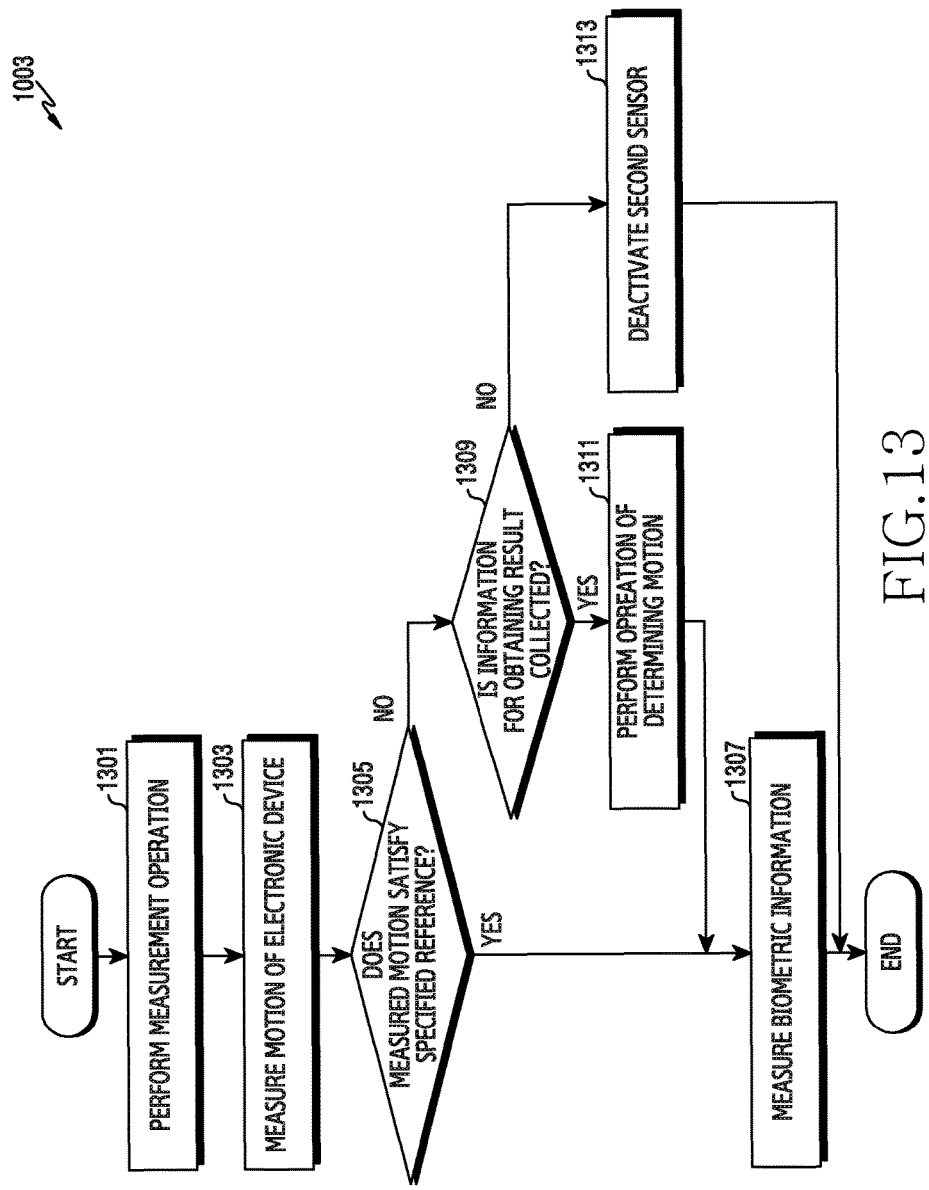
FIG. 13 is a flowchart illustrating the performance procedure of a method of changing a measurement parameter by an electronic device according to various embodiments of the present disclosure.

FIG. 13 is a flowchart illustrating the performance procedure of a method of changing a measurement parameter by an electronic device (e.g., the electronic device 101, the processor 120 of the electronic device 101, the processor 500, or the electronic device 400) according to various embodiments of the present disclosure.

Referring to FIG. 13, the performance procedure of the method of changing a measurement parameter may be a detailed operation for the operation 1003 illustrated in FIG. 10.

In operation 1301, the electronic device (e.g., the processor 120 or 500) may measure biometric information. According to an embodiment, the electronic device (e.g., the processor 120 or 500) may operate at least one second sensor to emit light for a selected (or specified) period of time and may acquire a signal output from the second sensor.

In operation 1303, the electronic device (e.g., the processor 120 or 500) may identify whether the motion of the electronic device is detected while the biometric information is being measured. According to various embodiments, the electronic device (e.g., the processor 120 or 500) may measure the motion of the electronic device based on at least one first sensor.

In operation 1305, the electronic device (e.g., the processor 120 or 500) may identify whether the measured motion satisfies a selected (or specified) reference. According to an embodiment, the measured motion may satisfy the selected (or specified) reference, which may indicate that a motion that does not affect the acquisition of biometric information is generated.

When the measured motion satisfies the selected (or specified) reference in operation 1305, the electronic device (e.g., the processor 120 or 500) may measure biometric information in operation 1307. According to various embodiments, the electronic device (e.g., the processor 120 or 500) may acquire information output from the second sensor based on a selected (or specified) measurement time.

When the measured motion does not satisfy the selected (or specified) reference in operation 1305, the electronic device (e.g., the processor 120 or 500) may determine whether information for obtaining a result is collected in operation 1309.

When the information for obtaining a result is collected in operation 1309, the electronic device (e.g., the processor 120 or 500) may perform an operation of determining the motion thereof in operation 1311. According to an embodiment, in order to prevent the measurement operation from being stopped at the time when the measurement is nearly completed, the electronic device (e.g., the processor 120 or 500) may not deactivate the second sensor even though the motion is generated and may perform the operation of determining the motion until the motion satisfies the selected (or specified) reference.

When the information for obtaining a result is not collected in operation 1309, the electronic device (e.g., the processor 120 or 500) may deactivate the second sensor in operation 1313. According to an embodiment, the electronic device (e.g., the processor 120 or 500) may determine that the motion that does not satisfy the selected (or specified) reference is generated in a state in which there is a predetermined period of time before the measurement is completed, and may accordingly stop measuring the biometric information.

According to various embodiments, at least one of the operations 1301 to 1313 may be omitted. For example, the operations 1309 and 1311 may be omitted. In this case, when it is determined in operation 1305 that the measured motion does not satisfy the selected (or specified) reference, the electronic device (e.g., the processor 120 or 500) may deactivate the second sensor in operation 1313. Furthermore, when it is determined in operation 1305 that the measured motion satisfies the selected (or specified) reference, the electronic device (e.g., the processor 120 or 500) may measure biometric information in operation 1307.

Figure 14:
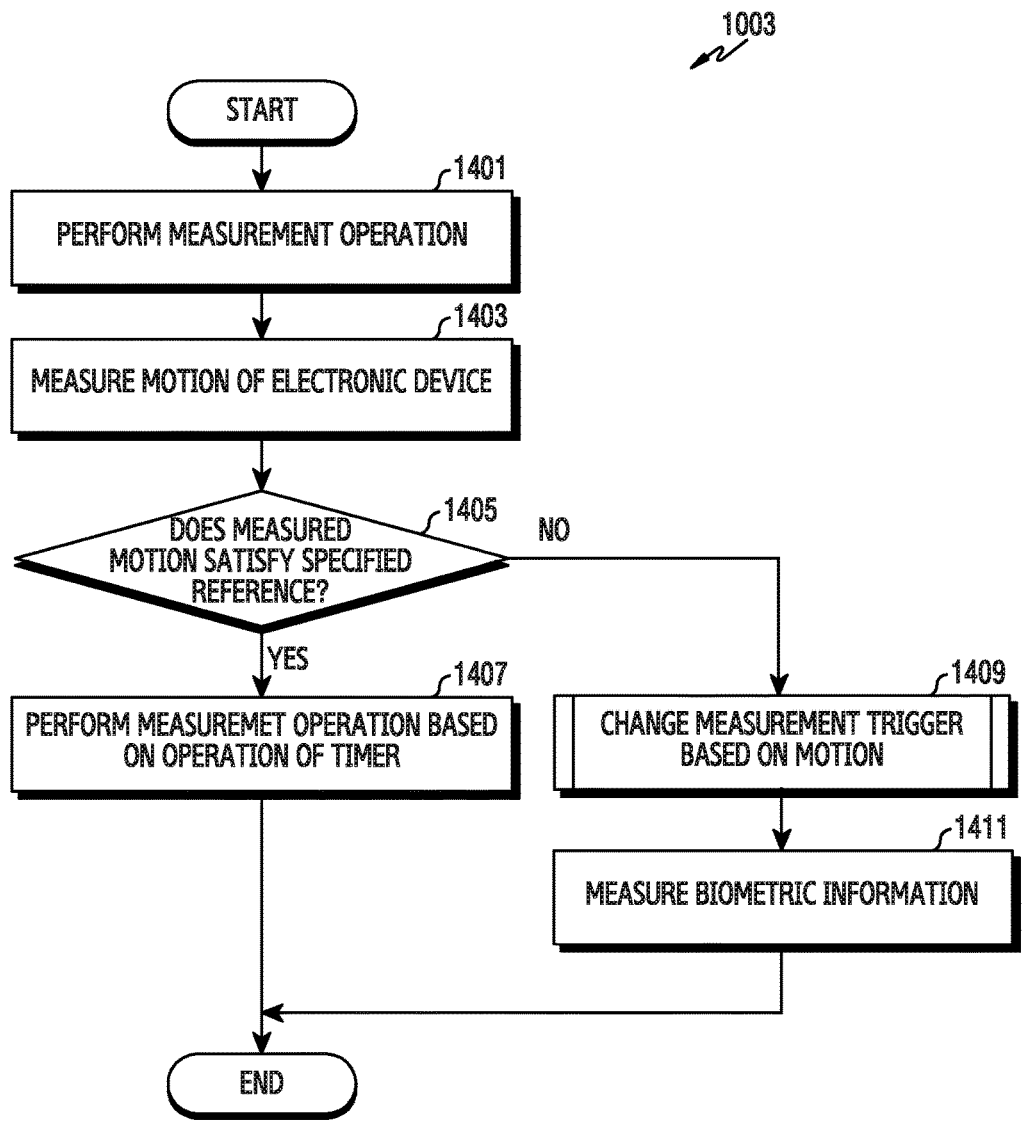
FIG. 14 is a flowchart illustrating the performance procedure of a method of changing a measurement parameter by an electronic device according to various embodiments of the present disclosure.

FIG. 14 is a flowchart illustrating the performance procedure of a method of changing a measurement parameter by an electronic device (e.g., the electronic device 101, the processor 120 of the electronic device 101, the processor 500, or the electronic device 400) according to various embodiments of the present disclosure.

Referring to FIG. 14, the performance procedure of the method of changing a measurement parameter may be a detailed operation for the operation 1003 illustrated in FIG. 10.

In operation 1401, the electronic device (e.g., the processor 120 or 500) may measure biometric information. According to an embodiment, the electronic device (e.g., the processor 120 or 500) may operate at least one second sensor to emit light for a selected (or specified) period of time and may acquire a signal output from the second sensor.

In operation 1403, the electronic device (e.g., the processor 120 or 500) may identify whether the motion of the electronic device is detected while the biometric information is being measured. According to various embodiments, the electronic device (e.g., the processor 120 or 500) may measure the motion of the electronic device based on at least one first sensor.

In operation 1405, the electronic device (e.g., the processor 120 or 500) may identify whether the measured motion satisfies a selected (or specified) reference. According to an embodiment, the measured motion may satisfy the selected (or specified) reference, which may indicate that a motion that does not affect the acquisition of biometric information is generated.

When the measured motion satisfies the selected (or specified) reference in operation 1405, the electronic device (e.g., the processor 120 or 500) may measure biometric information based on the operation of a timer in operation 1407. According to an embodiment, the electronic device (e.g., the processor 120 or 500) may attempt to measure biometric information according to a period having a selected (or specified) period of time.

When the measured motion does not satisfy the selected (or specified) reference in operation 1405, the electronic device (e.g., the processor 120 or 500) may change the measurement trigger based on the motion in operation 1409. According to an embodiment, the electronic device (e.g., the processor 120 or 500) may measure biometric information with a period having a selected (or specified) period of time as a trigger, but may not perform the measurement operation even though the measurement period arrives in a situation in which the motion that satisfies the selected (or specified) reference is not measured. For example, the electronic device (e.g., the processor 120 or 500) may identify whether the motion that satisfies the selected (or specified) reference is measured without performing the biometric information measurement operation, and when the motion that satisfies the selected (or specified) reference is detected, the electronic device may perform the biometric information measurement operation.

In operation 1411, the electronic device (e.g., the processor 120 or 500) may measure biometric information based on the changed measurement trigger. According to various embodiments, at least one of the operations 1401 to 1411 may be omitted.

Figure 15:
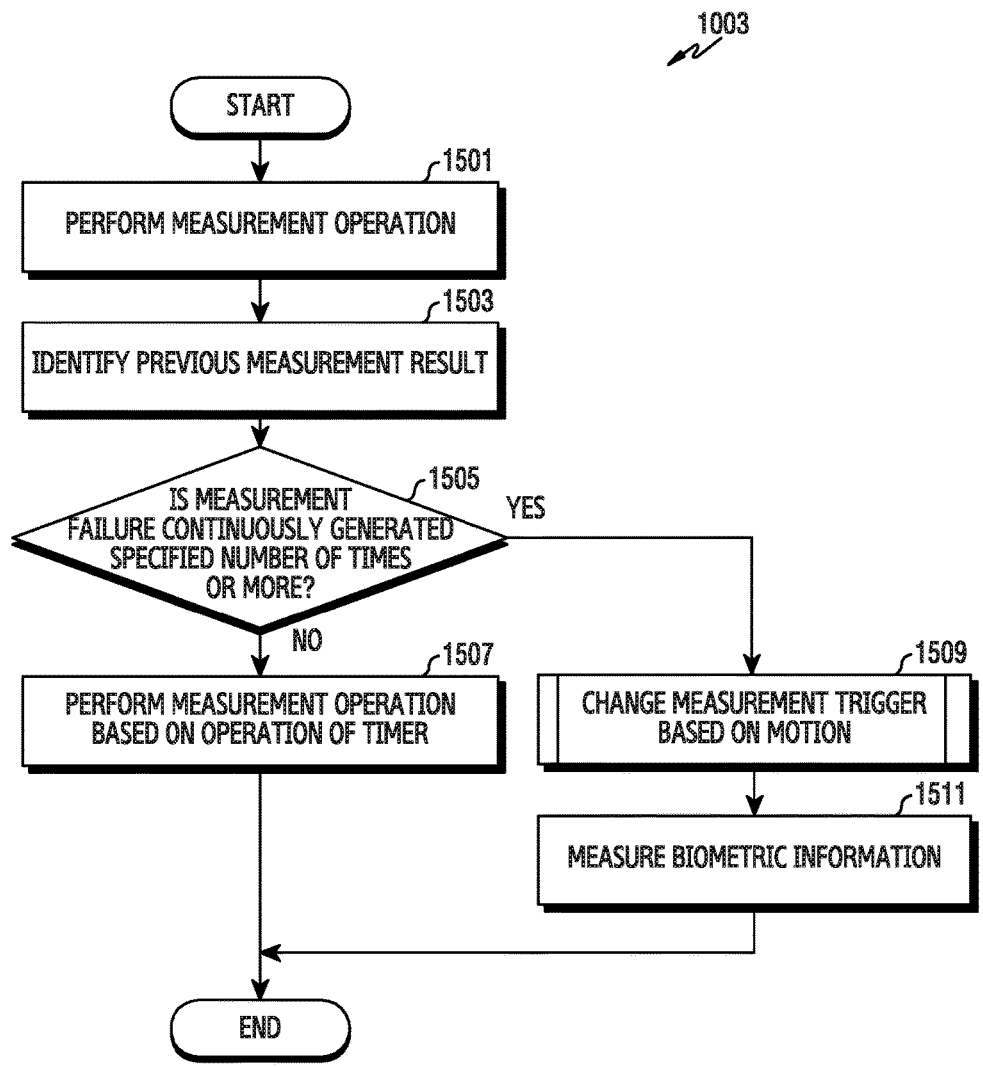
FIG. 15 is a flowchart illustrating the performance procedure of a method of changing a measurement parameter by an electronic device according to various embodiments of the present disclosure.

FIG. 15 is a flowchart illustrating the performance procedure of a method of changing a measurement parameter by an electronic device (e.g., the electronic device 101, the processor 120 of the electronic device 101, the processor 500, or the electronic device 400) according to various embodiments of the present disclosure.

Referring to FIG. 15, the performance procedure of the method of changing a measurement parameter may be a detailed operation for the operation 1003 illustrated in FIG. 10.

In operation 1501, the electronic device (e.g., the processor 120 or 500) may measure biometric information. According to an embodiment, the electronic device (e.g., the processor 120 or 500) may operate at least one second sensor to emit light for a selected (or specified) period of time and may acquire a signal output from the second sensor.

In operation 1503, the electronic device (e.g., the processor 120 or 500) may identify the previous measurement result while measuring the biometric information. The previous measurement result may be a result based on data acquired by at least one first sensor or at least one second sensor of the electronic device (e.g., the processor 120 or 500).

In operation 1505, the electronic device (e.g., the processor 120 or 500) may identify whether a measurement failure is continuously generated a selected (or specified) number of times or more based on the previous measurement result.

When it is identified in operation 1505 that the measurement failure is not continuously generated a selected (or specified) number of times or more, the electronic device (e.g., the processor 120 or 500) may perform the biometric information measurement operation based on the operation of a timer in operation 1507. According to an embodiment, the electronic device (e.g., the processor 120 or 500) may attempt to measure biometric information according to a period having a selected (or specified) period of time.

When it is identified in operation 1505 that the measurement failure is continuously generated a selected (or specified) number of times or more, the electronic device (e.g., the processor 120 or 500) may change the measurement trigger based on the motion in operation 1509. According to an embodiment, the electronic device (e.g., the processor 120 or 500) may identify whether the motion that satisfies the selected (or specified) reference is measured and may measure biometric information when the motion that satisfies the selected (or specified) reference is detected, instead of measuring biometric information with a period having a selected (or specified) period of time as a trigger.

In operation 1511, the electronic device (e.g., the processor 120 or 500) may measure biometric information based on the changed measurement trigger. According to various embodiments, at least one of the operations 1501 to 1511 may be omitted.

Figure 16:
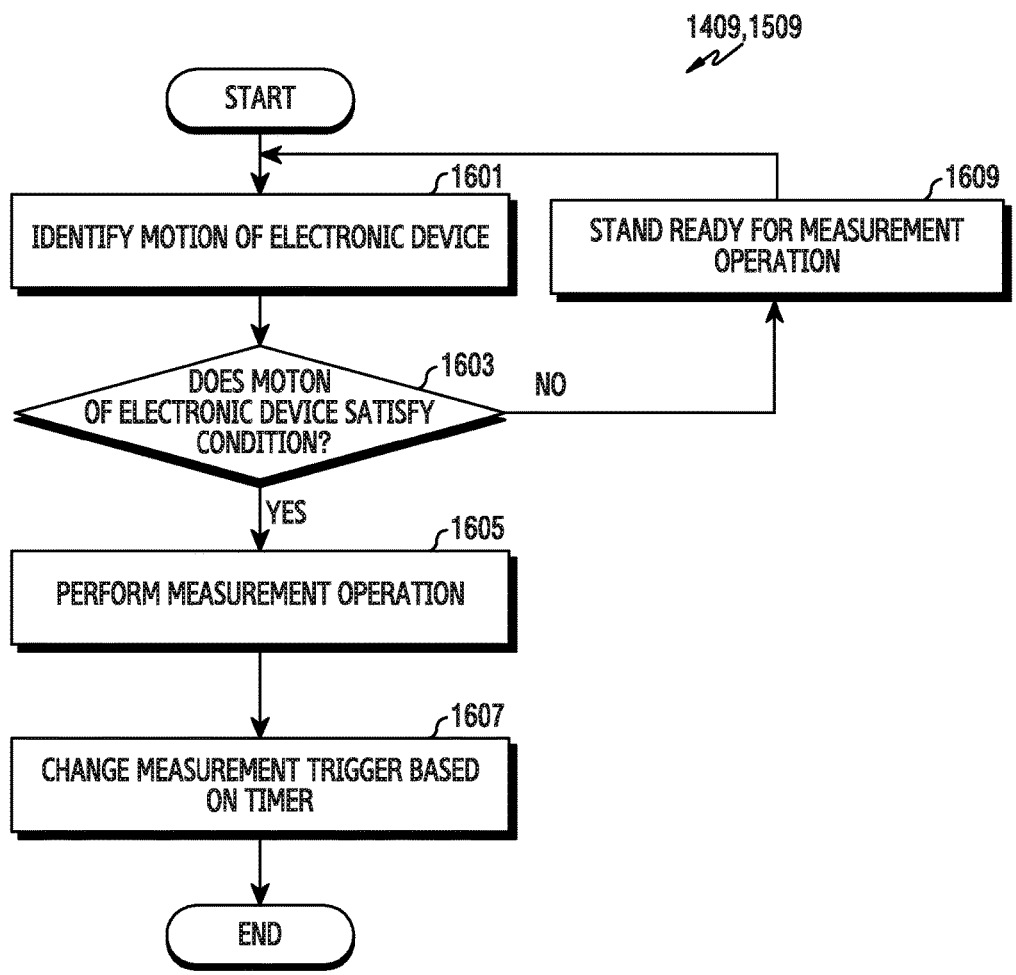
FIG. 16 is a flowchart illustrating the performance procedure of a method of changing a measurement trigger according to various embodiments of the present disclosure.

FIG. 16 is a flowchart illustrating the performance procedure of a method of changing a measurement trigger by an electronic device (e.g., the electronic device 101, the processor 120 of the electronic device 101, the processor 500, or the electronic device 400) according to various embodiments of the present disclosure.

Referring to FIG. 16, the performance procedure of the method of changing a measurement trigger may be a detailed operation for the operation 1409 illustrated in FIG. 14 or the operation 1509 illustrated in FIG. 15.

In operation 1601, the electronic device (e.g., the processor 120 or 500) may identify the motion of the electronic device. According to an embodiment, the electronic device (e.g., the processor 120 or 500) may measure the motion of the electronic device when the measurement trigger is changed based on the motion. For example, the electronic device (e.g., the processor 120 or 500) may measure the motion of the electronic device based on at least one first sensor.

In operation 1603, the electronic device (e.g., the processor 120 or 500) may identify whether the motion of the electronic device satisfies a condition. For example, the electronic device (e.g., the processor 120 or 500) may determine whether the motion that does not affect the measurement of biometric information is generated.

When the motion that satisfies the condition is not detected in operation 1603, the electronic device (e.g., the processor 120 or 500) may stand by without measuring biometric information in operation 1609. According to an embodiment, the electronic device (e.g., the processor 120 or 500) may stand by without performing the measurement operation until the motion that does not affect the measurement is detected. For example, when the measurement trigger is changed based on the motion, the electronic device (e.g., the processor 120 or 500) may not perform the measurement operation even though a measurement period arrives.

When the motion that satisfies the condition is detected in operation 1603, the electronic device (e.g., the processor 120 or 500) may measure biometric information in operation 1605.

In operation 1607, the electronic device (e.g., the processor 120 or 500) may change the measurement trigger based on a timer after measuring the biometric information based on the motion that satisfies the condition. According to an embodiment, the electronic device (e.g., the processor 120 or 500) may determine that the motion that does not affect the measurement is detected, and may accordingly change the measurement trigger to measure biometric information according to a period having a selected (or specified) period of time. According to various embodiments, at least one of the operations 1601 to 1609 may be omitted.

Figure 17:
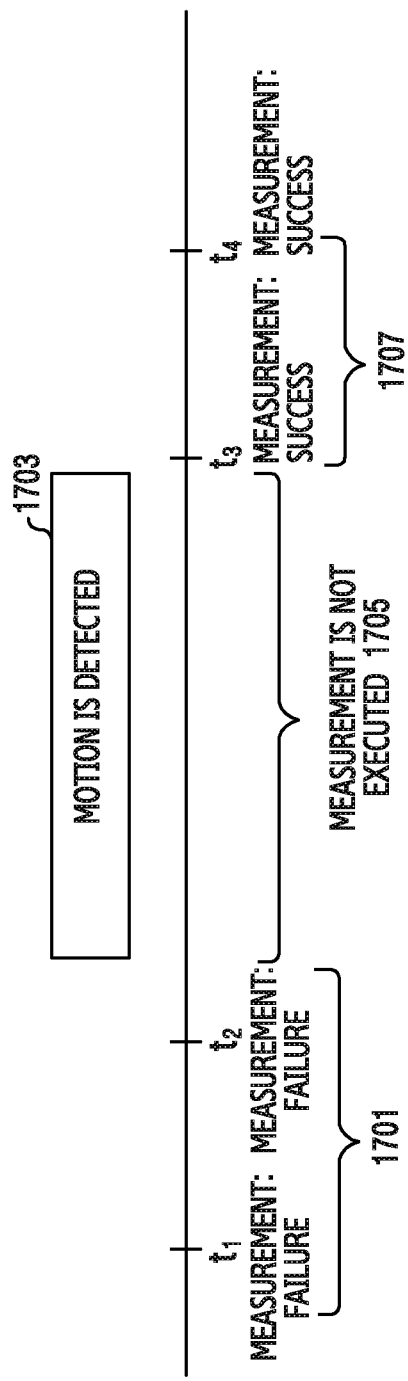
FIG. 17 is a view illustrating an operation of changing a measurement trigger by an electronic device according to various embodiments of the present disclosure.

FIG. 17 is a view illustrating an operation of changing a measurement trigger by an electronic device (e.g., the electronic device 101, the processor 120 of the electronic device 101, the processor 500, or the electronic device 400) according to various embodiments of the present disclosure.

Referring to FIG. 17, the electronic device (e.g., the processor 120 or 500) may attempt to measure biometric information according to a period having a selected (or specified) period of time (e.g., about 1 minute). For example, the electronic device (e.g., the processor 120 or 500) may measure biometric information with a selected (or specified) period as a measurement trigger.

According to various embodiments, the electronic device (e.g., the processor 120 or 500) may measure biometric information based on at least one second sensor when the selected (or specified) period arrives.

According to various embodiments, the electronic device (e.g., the processor 120 or 500) may change the measurement trigger when the motion of the electronic device does not satisfy a selected (or specified) condition (e.g., when the motion by which biometric information cannot be accurately measured is detected) at the time points t1 and t2 when the selected (or specified) period arrives. For example, the electronic device (e.g., the processor 120 or 500) may not perform the biometric information measurement operation until the motion by which biometric information can be accurately measured is detected. In other words, the electronic device (e.g., the processor 120 or 500) may measure biometric information with the motion satisfying the condition (e.g., the motion by which biometric information can be accurately measured) as the measurement trigger.

According to various embodiments, the electronic device (e.g., the processor 120 or 500) may change the measurement trigger when a measurement failure according to the motion is continuously generated (1701) a selected (or specified) number of times (e.g., about two times) or more.

For example, the electronic device (e.g., the processor 120 or 500) may monitor the motion by changing the measurement trigger based on the detection of the motion after the measurement failure is continuously generated a selected (or specified) number of times or more, and may perform the measurement operation at time t3 when the motion satisfies the selected (or specified) condition without performing the measurement operation (1705) based on the timer for the time interval 1703 for which the motion is detected. The electronic device (e.g., the processor 120 or 500) may change the measurement trigger based on the timer when the electronic device succeeds in acquiring biometric information. According to an embodiment, the electronic device (e.g., the processor 120 or 500) may change the measurement trigger to measure biometric information according to a period 1707 having a selected (or specified) period of time t3-t4 when the electronic device succeeds in acquiring biometric information by changing the measurement trigger based on the detection of the motion.

Figure 18:
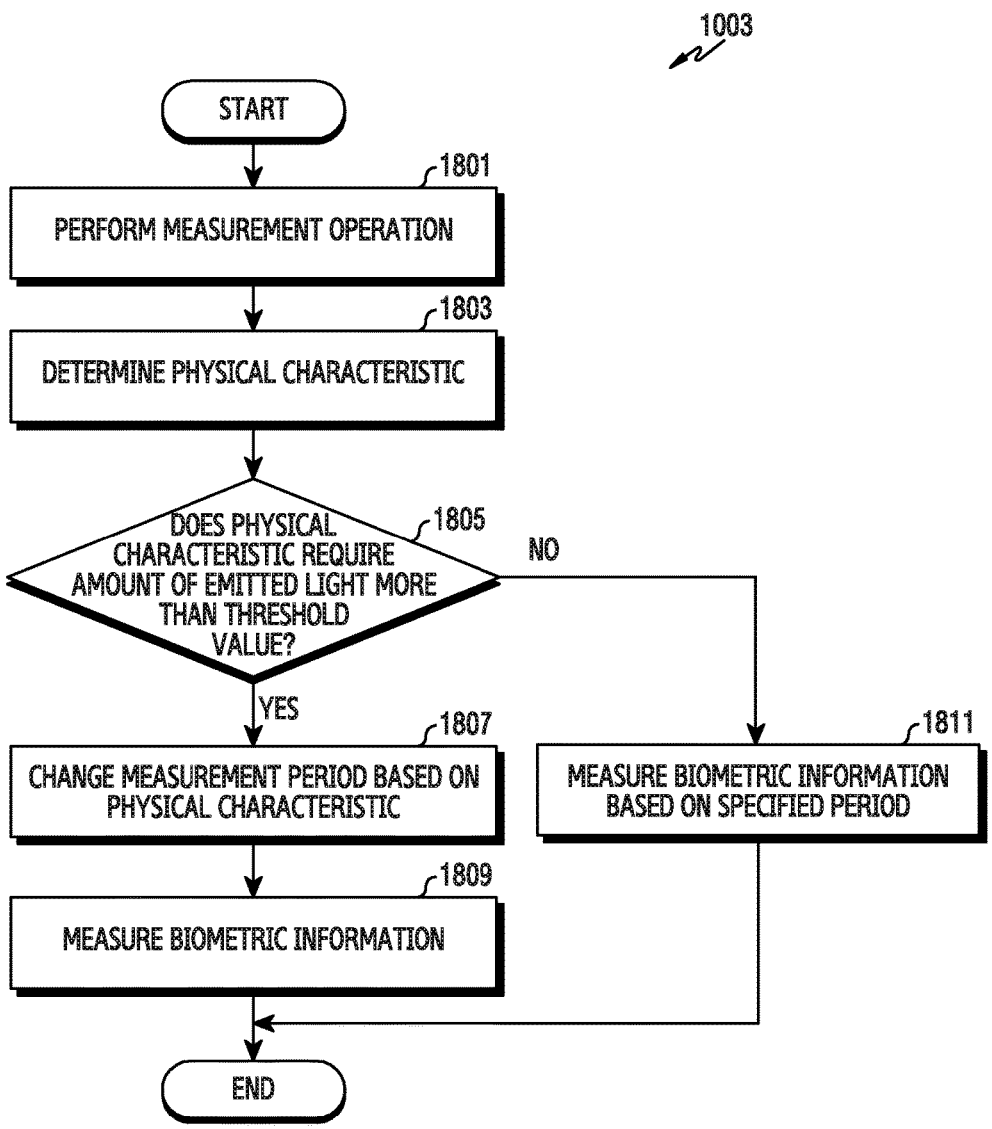
FIG. 18 is a flowchart illustrating the performance procedure of a method of changing a measurement parameter by an electronic device according to various embodiments of the present disclosure.

FIG. 18 is a flowchart illustrating the performance procedure of a method of changing a measurement parameter by an electronic device (e.g., the electronic device 101, the processor 120 of the electronic device 101, the processor 500, or the electronic device 400) according to various embodiments of the present disclosure.

Referring to FIG. 18, the performance procedure of the method of changing a measurement parameter may be a detailed operation for the operation 1003 illustrated in FIG. 10.

In operation 1801, the electronic device (e.g., the processor 120 or 500) may measure biometric information. According to an embodiment, the electronic device (e.g., the processor 120 or 500) may operate at least one second sensor to emit light for a selected (or specified) period of time and may acquire a signal output from the second sensor.

In operation 1803, the electronic device (e.g., the processor 120 or 500) may determine a characteristic of a body with which the second sensor makes contact. According to an embodiment, the electronic device (e.g., the processor 120 or 500) may determine a physical characteristic of an object for which biometric information is measured. According to an embodiment, the electronic device (e.g., the processor 120 or 500) may determine the skin color of the body with which the second sensor makes contact as the physical characteristic.

In operation 1805, the electronic device (e.g., the processor 120 or 500) may determine whether the physical characteristic uses an amount of emitted light more than a threshold value. According to various embodiments, the electronic device (e.g., the processor 120 or 500) may measure a melanin index based on the amount of reflected light that is received by a light-receiving part of the second sensor, and may identify the skin color and the amount of emitted light of a light-emitting part that is used during measurement based on the measured melanin index. For example, the amounts of emitted light according to melanin indices may be defined as listed in Table 2 below.

TABLE 2

| Melanin Index | Type of skin color | Current intensity |
|---|---|---|
| 5-10 | Very light | 31~40% |
| 11-20 | Light | 41~50% |
| 21-30 | Intermediate | 51~60% |
| 31-40 | Tan | 61~70% |
| 41-70 | Brown | 71~80% |
| 71-99 | black | 81~100% |

For example, a higher melanin index represents a darker skin color, and the electronic device (e.g., the processor 120 or 500) may determine that a larger amount of power is consumed for a darker skin color than for a lighter skin color.

According to various embodiments, the electronic device (e.g., the processor 120 or 500) may store a user's physical characteristic, or receive the same from an external device.

When it is determined in operation 1805 that the physical characteristic does not require an amount of emitted light more than the threshold value, the electronic device (e.g., the processor 120 or 500) may measure biometric information based on a selected (or specified) measurement period in operation 1811.

When it is determined in operation 1805 that the physical characteristic uses an amount of emitted light more than the threshold value, the electronic device (e.g., the processor 120 or 500) may change the measurement period based on the physical characteristic in operation 1807. For example, the electronic device (e.g., the processor 120 or 500) may increase the measurement period to reduce the number of measurements when an amount of emitted light more than the threshold value is used when biometric information is measured.

When the measurement period is changed in operation 1807, the electronic device (e.g., the processor 120 or 500) may measure biometric information based on the changed measurement period in operation 1809. According to various embodiments, at least one of the operations 1801 to 1811 may be omitted.

Figure 19:
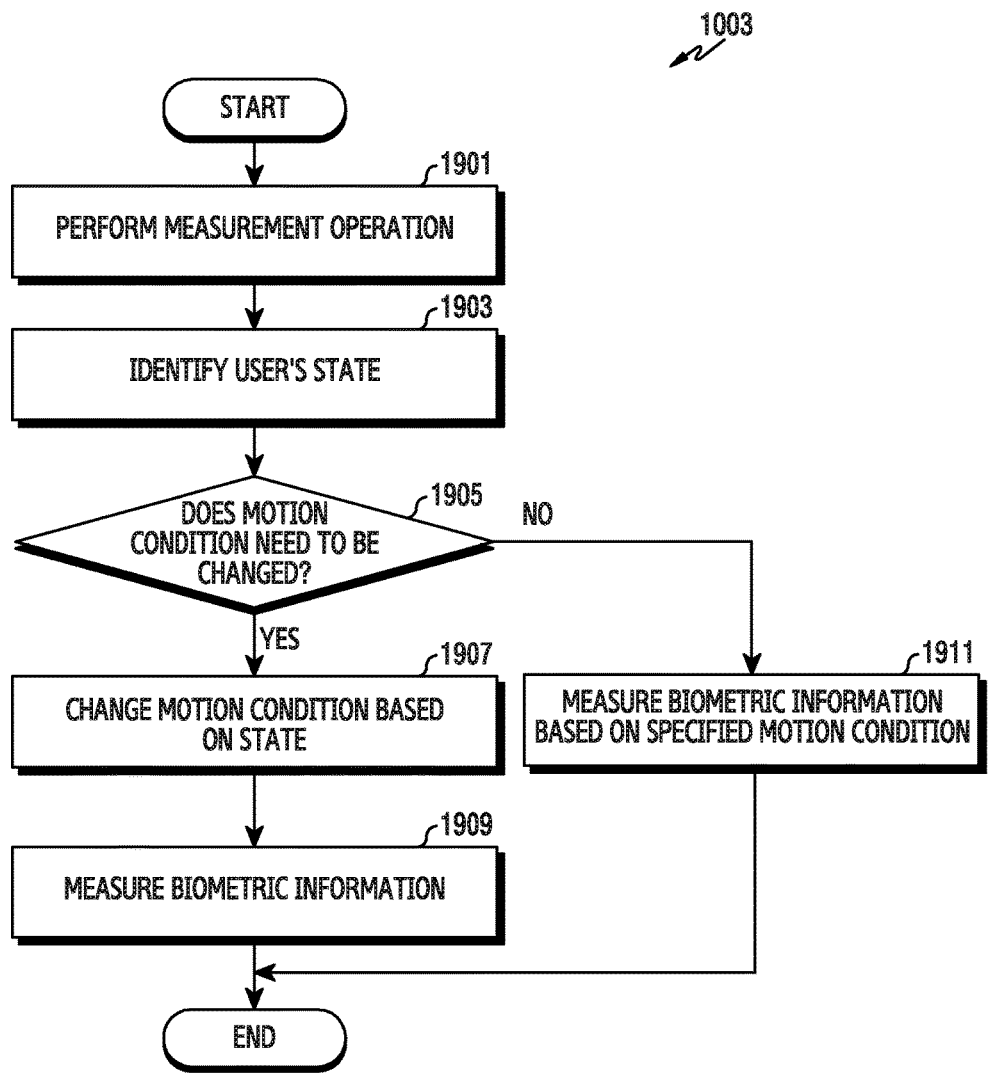
FIG. 19 is a flowchart illustrating the performance procedure of a method of changing a measurement parameter by an electronic device according to various embodiments of the present disclosure.

FIG. 19 is a flowchart illustrating the performance procedure of a method of changing a measurement parameter by an electronic device (e.g., the electronic device 101, the processor 120 of the electronic device 101, the processor 500, or the electronic device 400) according to various embodiments of the present disclosure.

Referring to FIG. 19, the performance procedure of the method of changing a measurement parameter may be a detailed operation for the operation 1003 illustrated in FIG. 10.

In operation 1901, the electronic device (e.g., the processor 120 or 500) may measure biometric information. According to an embodiment, the electronic device (e.g., the processor 120 or 500) may operate at least one second sensor to emit light for a selected (or specified) period of time and may acquire a signal output from the second sensor.

In operation 1903, the electronic device (e.g., the processor 120 or 500) may identify a user's state. According to an embodiment, the electronic device (e.g., the processor 120 or 500) may identify the user's state, such as a sleep state, an active state, etc.

In operation 1905, the electronic device (e.g., the processor 120 or 500) may determine whether a motion condition needs to be changed. According to various embodiments, when the user is in a sleep state, the motion condition may not be required since it may be determined that there is no motion, or the strength of a motion is low. When the motion condition is not required, it may be determined that the motion condition needs to be changed.

When it is determined in operation 1905 that the motion condition does not need to be changed, the electronic device (e.g., the processor 120 or 500) may measure biometric information based on a selected (or specified) motion condition in operation 1911.

When it is determined in operation 1905 that the motion condition needs to be changed, the electronic device (e.g., the processor 120 or 500) may change the motion condition based on the user's state in operation 1907. For example, the electronic device (e.g., the processor 120 or 500) may omit the condition for determining a motion, or may decrease a desired motion reference value.

When the motion condition is changed in operation 1907, the electronic device (e.g., the processor 120 or 500) may measure biometric information based on the changed motion condition in operation 1909. According to various embodiments, at least one of the operations 1901 to 1911 may be omitted.

Figure 20:
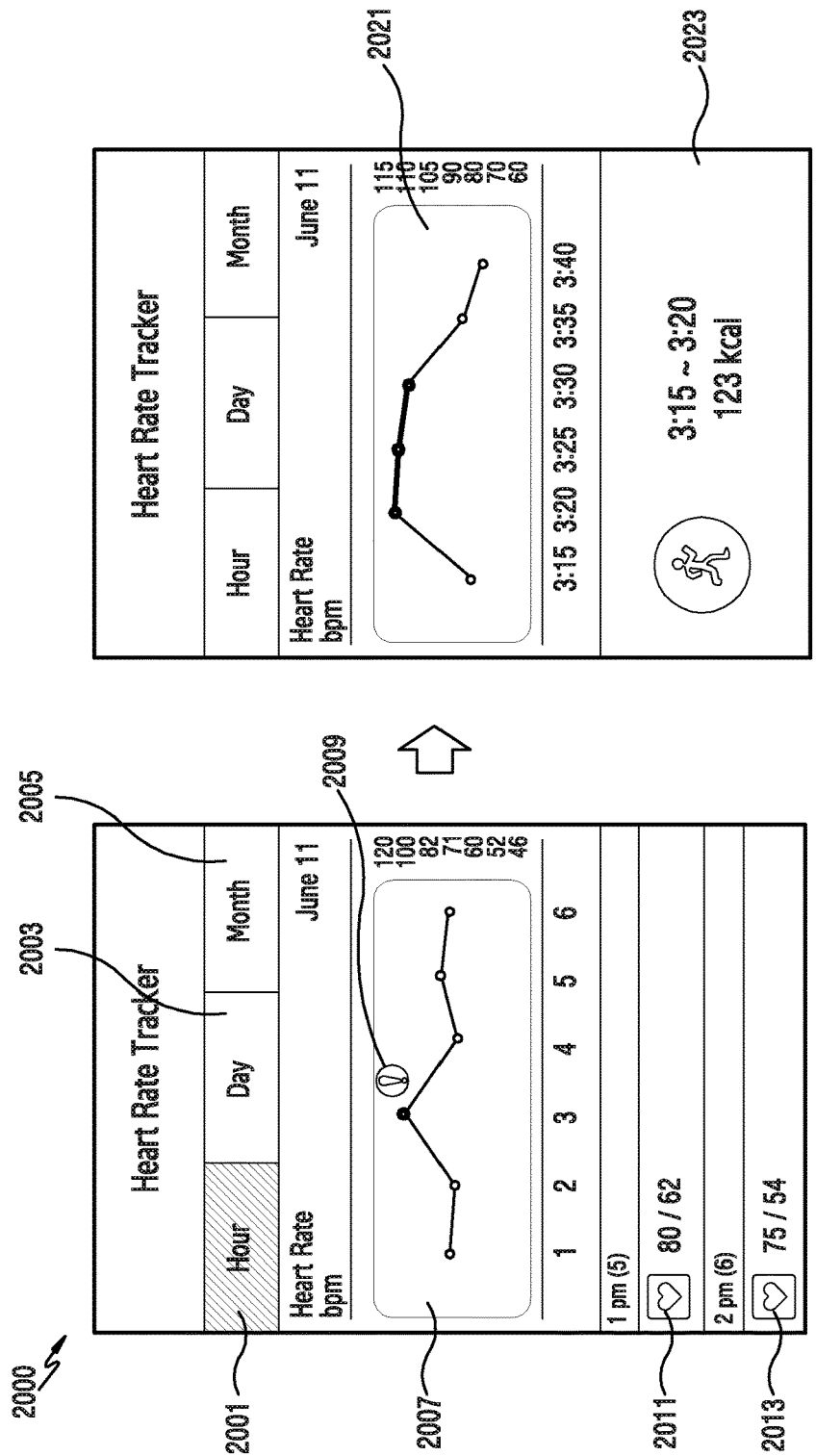
FIG. 20 is a view illustrating a screen configuration of an electronic device according to various embodiments of the present disclosure.

FIG. 20 is a view illustrating a screen configuration of an external electronic device (e.g., a smart phone) that is connected to an electronic device (e.g., the electronic device 101 or 400) through wireless or wired communication according to various embodiments of the present disclosure.

Referring to FIG. 20, the electronic device (e.g., the processor 120 or 500) may store biometric information (e.g., heart rate information), which is measured at every selected (or specified) period, in a memory and may display the measurement result 2000 on the screen thereof based on an input.

According to various embodiments, the electronic device (e.g., the processor 120 or 500) may display the measured heart rate information in units of hours 2001, days 2003, and months 2005. According to an embodiment, when displaying the measurement result in units of hours, the electronic device (e.g., the processor 120 or 500) may display the average value of the heart rate information measured at every hour in units of hours. According to another embodiment, when displaying the measurement result in units of days, the electronic device (e.g., the processor 120 or 500) may display the average value of the heart rate information measured at every day in units of days. According to yet another embodiment, when displaying the measurement result in units of months, the electronic device (e.g., the processor 120 or 500) may display the average value of the heart rate information measured at every month in units of months. According to various embodiments, the electronic device (e.g., the processor 120 or 500) may also display the highest and lowest values 2011 and 2013 of the heart rate information that is displayed in units of hours, as well as the average value of the heart rate information.

According to various embodiments, when displaying (2007) the result of the heart rate information, the electronic device (e.g., the processor 120 or 500) may display an indicator together for the time point at which the average value is higher or lower than a predetermined reference. For example, the electronic device (e.g., the processor 120 or 500) may display the indicator using a selected (or specified) color, a selected (or specified) text, a selected (or specified) icon, or the like. In the drawing, an exclamation mark 2009 displayed in the time interval between 3 hour and 4 hour may be an indicator that represents that heart rate information more than the average value is measured.

According to various embodiments, when an input for the indicator is detected, the electronic device (e.g., the processor 120 or 500) may display detailed information relating to the corresponding time interval. For example, the electronic device (e.g., the processor 120 or 500) may display the heart rate information 2021 that corresponds to the time interval relevant to the indicator for which the input is detected and the state information 2023 (e.g., calorie consumption, etc.) of the electronic device or a user for the corresponding time interval together. The drawing illustrates that the user practiced running from 3:15 to 3:20 so that the user's heart rate increased.

A method of operating an electronic device, according to various embodiments, may include: determining whether the electronic device is worn on a part of the user's body using at least one first sensor (e.g., at least one of a proximity sensor, an acceleration sensor, a gyro sensor, and a terrestrial magnetism sensor); acquiring information on the motion of the electronic device using at least a part of the at least one first sensor for a second period of time shortly before and/or immediately after a first period of time selected (or specified) passes from the time when the electronic device is worn on a part of the user's body; and activating (operating or triggering) at least one second sensor (e.g., a heart rate sensor) based on at least a part of the information on the motion.

According to various embodiments, the second period of time may be shorter than the first period of time.

According to various embodiments, the at least one second sensor may include a biometric sensor.

According to various embodiments, the biometric sensor may include at least one of a heart rate sensor, a blood pressure sensor, an ECG sensor, a skin moisture sensor, and an oxygen saturation sensor.

According to various embodiments, the activating (operating or triggering) may include: acquiring additional information on the motion of the electronic device using at least a part of the at least one first sensor for a third period of time, which is shorter than the first period of time, immediately after the second period of time passes; and activating (operating or triggering) the at least one second sensor based on at least a part of the additional information in a case where the information on the motion does not satisfy a selected condition.

According to various embodiments, at least one of the second period of time and the third period of time may include the time point when the first period of time passes.

According to various embodiments, the second period of time may include the time point when the first period of time passes.

According to various embodiments, the activating (operating or triggering) may include: when data is not received from the activated (operated or triggered) second sensor within a selected (or specified) time, activating (operating or triggering) the second sensor again after the selected (specified) time passes.

According to various embodiments, the activating (operating or triggering) may include: acquiring additional information on the motion of the electronic device using at least a part of the at least one first sensor for a period of time that is substantially the same as the second period of time before the selected (or specified) time passes; and activating (operating or triggering) the at least one second sensor again based on at least a part of the additional information.

According to various embodiments, the method of operating the electronic device may further include: acquiring data from at least one of the at least one first sensor and the at least one second sensor; and changing the first period of time and/or the second period of time and/or the third period of time based on at least a part of the acquired data.

According to various embodiments, the method of operating the electronic device may further include: acquiring data from at least one of the at least one first sensor and the at least one second sensor; and changing at least one condition for activating (operating or triggering) the at least one second sensor based on at least a part of the data.

According to various embodiments, the method of operating the electronic device may further include: acquiring data from at least one of the at least one first sensor and the at least one second sensor; and changing at least one of a period of time and a sampling rate for activating (operating or triggering) the at least one second sensor based on at least a part of the data.

A method of operating an electronic device, according to various embodiments, includes: determining whether the electronic device is worn on a part of a user's body using at least one first sensor; activating (operating or triggering) at least one second sensor based on at least a part of the measured motion of the electronic device within a selected (or specified) time range when a selected (or specified) period of time passes from the time when the electronic device is worn on the user's body part; and measuring biometric information based on the at least one second sensor.

According to various embodiments, the at least one first sensor may include at least one of a proximity sensor, a gyro sensor, a terrestrial magnetism sensor, and an acceleration sensor.

According to various embodiments, the method may include: acquiring additional information on the motion of the electronic device using at least a part of the at least one first sensor for a selected (or specified) time from the time when the period of time passes; and activating (operating or triggering) the at least one second sensor based on at least a part of the additional information, without activating (operating or triggering) the second sensor when at least a part of the motion does not satisfy a selected (or specified) condition.

According to various embodiments, the measuring of the biometric information based on the at least one second sensor may include: accumulating the number of failures when the measurement of the biometric information fails; and deactivating the second sensor when the cumulative number of failures satisfies a selected (or specified) condition.

According to various embodiments, the measuring of the biometric information based on the at least one second sensor may include: acquiring data from at least one of the at least one first sensor and the at least one second sensor; and changing at least one condition for activating (operating or triggering) the at least one second sensor based on at least a part of the data.

According to various embodiments, the measuring of the biometric information based on the at least one second sensor may include: acquiring data from at least one of the at least one first sensor and the at least one second sensor; and changing at least one of a period of time or a sampling rate for activating (operating or triggering) the at least one second sensor based on at least a part of the data.

According to various embodiments, the measuring of the biometric information based on the at least one second sensor may include: acquiring data about the user's physical characteristic (e.g., skin color) or state (e.g., a sleep state or an active state); and changing at least one condition for activating (operating or triggering) the at least one second sensor based on at least a part of the data.

According to various embodiments, the acquiring of the additional information on the motion may include changing the selected (or specified) time for acquiring the additional information based on data acquired from at least one of the at least one first sensor and the at least one second sensor.

According to an embodiment, a method of operating an electronic device may include: determining whether the electronic device is close to a user's body; acquiring information on the motion of the electronic device using at least one first sensor within a selected (or specified) time range from the time when a selected (or specified) period passes in a case where the electronic device is close to the user's body part; and acquiring the user's biometric information through at least one second sensor based on at least a part of the information on the motion.

The electronic device and the method, according to the various embodiments of the present disclosure, can selectively operate a biometric sensor based on a selected (or specified) condition, thereby measuring biometric information while reducing power consumption.

Further, the electronic device and the method, according to the various embodiments of the present disclosure, can operate a biometric sensor according to a selected (or specified) period, thereby continually measuring biometric information.

In addition, the electronic device and method, according to the various embodiments of the present disclosure, can measure the motion of the electronic device and can selectively measure a user's biometric information based on the measured motion, thereby improving the accuracy of the measured biometric information.

A terminology "module" used for the present disclosure may mean, for example, a unit including a combination of one or two or more among a hardware, a software, or a firmware. A "module" may be interchangeably used with a terminology such as a unit, a logic, a logical block, a component, or a circuit, etc. A "module" may be a minimum unit of an integrally configured part or a portion thereof. A "module" may be a minimum unit performing one or more functions or a portion thereof. A "module" may be mechanically or electronically implemented. For example, a "module" according to the present disclosure may include at least one of an application-specific IC (ASIC) chip, a field-programmable gate arrays (FPGAs), or a programmable-logic device which are known, or to be developed in the future, and performing certain operations.

According to various embodiments, at least a portion of an apparatus (e.g., modules or functions thereof) or a method (e.g., operations) according to the present disclosure may be implemented as an instruction stored in a non-transitory computer-readable storage media, for example, in the form of a programming module. An instruction, when executed by one or more processors (e.g., the processor 120), may configure the one or more processors to perform a function corresponding to the instruction. The non-transitory computer-readable storage media may be, for example, the memory 130. At least a portion of a programming module may be implemented (e.g., executed) by, for example, the processor 120. At least a portion of the programming module may include, for example, a module, a program, a routine, sets of instructions, or a process, etc. for performing one or more functions.

The non-transitory computer-readable storage media may include a hard disk, a magnetic media such as a floppy disk and a magnetic tape, compact disc ROM (CD-ROM), optical media such as DVD, magneto-optical media such as a floptical disk, and a hardware device specially configured for storing and performing a program instruction (e.g., a programming module) such as ROM, RAM, a flash memory, etc. Also, the program instruction may include not only a machine language code generated by a compiler but also a high-level language code executable by a computer using an interpreter, etc. The above-described hardware device may be configured to operate as one or more software modules in order to perform an operation of the present disclosure, and vice versa.

A module or a programming module according to the present disclosure may include at least one of the above-described elements, omit a portion thereof, or further include additional other elements. Operations performed by a module, a programming module, or other elements according to the present disclosure may be executed in a sequential, parallel, or heuristic method. Also, a portion of the operations may be executed in a different sequence, omitted, or other operations may be added.

While the present disclosure has been shown and described with reference to various embodiments thereof, it will be understood by those skilled in the art that various changes in form and details may be made therein without departing from the spirit and scope of the present disclosure as defined by the appended claims and their equivalents.

What is claimed is:

1. An electronic device comprising:
   a housing;
   a fastener coupled to a part of the housing and detachably attachable to a part of a user's body;
   at least one first sensor;
   at least one second sensor;
   a memory; and
   at least one processor electrically connected to the at least one first sensor, the at least one second sensor, and the memory,
   wherein the memory stores one or more computer programs including instructions which, when executed by the at least one processor, cause the at least one processor to:
      determine whether the electronic device is worn on the part of the user's body using the at least one first sensor,
      acquire first information on a motion of the electronic device using at least a part of the at least one first sensor for a second period of time shortly before and/or immediately after a first period of time, when the at least one processor determines that the electronic device is worn on a part of the user's body,
      activate the at least one second sensor based on at least a part of the first information on the motion,
      detect a biometric information of the user using the activated at least one second sensor,
      during detecting the biometric information, acquire second information on a motion of the electronic device using at least the part of the at least one first sensor, and
      in response to identifying that the motion of the electronic device included in the second information is more than a threshold motion, inactivate the at least one second sensor.

2. The electronic device of claim 1, wherein the second period of time is shorter than the first period of time.

3. The electronic device of claim 1, wherein the at least one second sensor comprises a biometric sensor.

4. The electronic device of claim 3, wherein the biometric sensor comprises at least one of a heart rate sensor, a blood pressure sensor, an electrocardiogram sensor, a skin moisture sensor, or an oxygen saturation sensor.

5. The electronic device of claim 1, wherein when the first information on the motion does not satisfy a selected condition, the instructions which, when executed by the at least one processor, further cause the at least one processor to:
   acquire additional information on the motion of the electronic device using at least a part of the at least one first sensor for a third period of time, which is shorter than the first period of time, immediately after the second period of time passes; and
   activate the at least one second sensor based on at least a part of the additional information.

6. The electronic device of claim 5, wherein at least one of the second period of time or the third period of time comprises a time point when the first period of time passes.

7. The electronic device of claim 1, wherein the second period of time comprises a time point when the first period of time passes.

8. The electronic device of claim 1, wherein, when data is not received from the activated second sensor within a selected time, the instructions further configure the at least one processor to activate the second sensor again after the selected time passes.

9. The electronic device of claim 8, wherein the instructions further configure the at least one processor to:
   acquire additional information on the motion of the electronic device using at least a part of the at least one first sensor for a period of time that is substantially the same as the second period of time before the selected time passes; and
   activate the at least one second sensor again based on at least a part of the additional information.

10. The electronic device of claim 1, wherein the instructions further configure the at least one processor to:
    acquire data from at least one of the at least one first sensor and the at least one second sensor; and
    change at least one of the first period of time, the second period of time, and the third period of time based on at least a part of the acquired data.

11. The electronic device of claim 1, wherein the instructions further configure the at least one processor to:
    acquire data from at least one of the at least one first sensor and the at least one second sensor; and
    change at least one condition for activating the at least one second sensor based on at least a part of the data.

12. The electronic device of claim 1, wherein the instructions further configure the at least one processor to:
    acquire data from at least one of the at least one first sensor and the at least one second sensor; and
    change at least one of a period of time and a sampling rate for activating the at least one second sensor based on at least a part of the data.

13. A method comprising:
    determining whether an electronic device is worn on a part of a user's body using at least one first sensor of the electronic device;
    acquiring first information on a motion of the electronic device using at least a part of the at least one first sensor for a second period of time shortly before and/or immediately after a first period of time when it is determined that the electronic device is worn on a part of the user's body;
    activating at least one second sensor based on at least a part of the first information on the motion of the electronic device;
    detecting a biometric information of the user using the activated at least one second sensor;
    during detecting the biometric information, acquiring second information on a motion of the electronic device using at least the part of the at least one first sensor; and
    in response to identifying that the motion of the electronic device included in the second information is more than a threshold motion, inactivating the at least one second sensor.

14. The method of claim 13, wherein the at least one first sensor comprises at least one of a proximity sensor, a gyro sensor, a terrestrial magnetism sensor, or an acceleration sensor.

15. The method of claim 13, further comprising:
    acquiring additional information on the motion of the electronic device using at least a part of the at least one first sensor for a third period of time, which is shorter than the first period of time, immediately after the second period of time passes; and
    activating the at least one second sensor based on at least a part of the additional information.

16. The method of claim 15, wherein at least one of the second period of time or the third period of time comprises a time point when the first period of time passes.

17. The method of claim 13, further comprising:
accumulating a number of failures when the detection of the biometric information fails; and
deactivating the at least one second sensor when a cumulative number of failures satisfies a selected condition.

18. The method of claim 13, wherein the detection of the biometric information of the user using the activated at least one second sensor comprises:
acquiring data about a physical characteristic or state of the user; and
changing at least one condition for activating the at least one second sensor based on at least a part of the data.

19. The method of claim 13, wherein the detection of the biometric information of the user using the activated at least one second sensor comprises:
acquiring data from at least one of the at least one first sensor and the at least one second sensor; and
changing at least one condition for activating the at least one second sensor based on at least a part of the data.

20. An electronic device comprising:
at least one first sensor;
at least one second sensor;
a memory; and
at least one processor electrically connected to the at least one first sensor, the at least one second sensor, and the memory,
wherein the memory stores one or more computer programs including instructions which, when executed by the at least one processor, cause the at least one processor to:
determine whether the electronic device is worn on a part of a user's body,
when the electronic device is worn on the part of the user's body, determine a motion of the electronic device based on first information obtained by the at least one first sensor,
determine whether to identify biometric information based on the motion of the electronic device,
in response to determining to identify biometric information, identify the biometric information of the user through the at least one second sensor,
during identifying the biometric information of the user, obtain second information on a motion of the electronic device using the at least one first sensor, and
in response to identifying that the motion of the electronic device included in the second information is more than a threshold motion, inactivate the at least one second sensor.

\* \* \* \* \*